United States Patent [19]

Ralph et al.

[11] Patent Number: 5,567,611
[45] Date of Patent: Oct. 22, 1996

[54] MULTIFUNCTIONAL M-CSF PROTEINS AND GENES ENCODING THEREFOR

[75] Inventors: Peter Ralph, Orinda; George Martin, Berkeley; Michael Piatak, Pleasanton; James W. Larrick, Woodside, all of Calif.

[73] Assignee: Cetus Onocology Corporation, Emeryville, Calif.

[21] Appl. No.: 354,456

[22] Filed: Dec. 12, 1994

Related U.S. Application Data

[63] Continuation of Ser. No. 995,338, Dec. 21, 1992, abandoned, which is a continuation of Ser. No. 340,228, Apr. 19, 1989, abandoned.

[51] Int. Cl.$^6$ ............ C12N 15/00; C12N 15/24; C12N 15/20; C12N 15/27
[52] U.S. Cl. ............ 435/240.2; 435/69.51; 435/69.52; 435/69.7; 435/252.3; 435/320.1; 536/23.4; 536/23.5; 536/23.52
[58] Field of Search ............ 536/23.5, 23.4, 536/23.52; 435/6, 69.51, 69.52, 69.7, 240.2, 252.3, 320.1, 172.3

[56] References Cited

U.S. PATENT DOCUMENTS

| | | | |
|---|---|---|---|
| 4,468,382 | 8/1984 | Bacha et al. | 424/177 |
| 4,518,584 | 5/1985 | Mark et al. | 424/85 |
| 4,545,985 | 10/1985 | Pastan et al. | 424/85 |
| 4,675,382 | 6/1987 | Murphy | 530/350 |
| 4,703,008 | 10/1987 | Lin | 435/240.2 |
| 4,738,927 | 4/1988 | Taniguchi et al. | 435/243 |
| 4,752,585 | 6/1988 | Koths et al. | 435/256 |
| 4,758,428 | 7/1988 | Mark et al. | 424/85 |
| 4,762,791 | 8/1988 | Goeddel et al. | 435/243 |
| 4,762,914 | 8/1988 | Auron et al. | 530/351 |
| 4,778,879 | 10/1988 | Mertelsmann et al. | 530/351 |
| 4,929,700 | 5/1990 | Halenbeck et al. | 530/351 |
| 5,013,653 | 5/1991 | Huston et al. | 435/69.7 |
| 5,084,556 | 1/1992 | Brown | 530/351 |
| 5,171,675 | 12/1992 | Cerretti et al. | 435/69.5 |

FOREIGN PATENT DOCUMENTS

| | | | |
|---|---|---|---|
| 6675686 | 6/1987 | Australia. | |
| 0088195 | 9/1983 | European Pat. Off. | C12N 15/00 |
| 0091539 | 10/1983 | European Pat. Off. | C12N 15/00 |
| 0109748 | 5/1984 | European Pat. Off. | C12N 15/00 |
| 0225579 | 6/1987 | European Pat. Off. | A61K 37/02 |
| 0256843 | 2/1988 | European Pat. Off. | C12N 15/00 |
| 0261592 | 3/1988 | European Pat. Off. | C12N 15/00 |
| 0272779 | 6/1988 | European Pat. Off. | C12P 21/02 |
| 61-128889 | 6/1986 | Japan | C07H 21/04 |
| 8604606 | 8/1986 | WIPO | C12N 15/00 |
| 8706954 | 11/1987 | WIPO | C12P 21/00 |

OTHER PUBLICATIONS

Habermann, P., Inpadoc abstract for EPO 288809 (Nov. '88).
Habermann, P., Derwent abstract for EPO 288809 (Nov. '88).
Tonouchi et al., 1988, *J. Biochem.*, 104:30–34.
Sideras et al., 1988, *Immunological Reviews*, 102:189–212.
Kaushansky et al., 1986, *PNAS (USA)*, 83:3101–3105.
Feng, G-S. et al., 1988, *Science* 241:1501–1503.
Kelley, V. E. et al., 1988, *Proc. Natl. Acad. Sci. USA* 85:3980–3984.
Ralph, P. et al., 1986, *Blood* 68:633–639.
Pirker, R. et al. 1985, *J. Clin. Invest.* 76:1261–1267.
Veronese, F. et al., 1985, *Applied Biochem. & Biotech* 11:141–152.
Ralph, P. et al., in *The Year in Immunology* 1988, Cruse et al., eds., Basel, Karger, 1989, vol. 5, pp. 103–125.
Ralph, P. "Colony Stimulating Factors", in *Human Monocytes*, Asherson et al. eds., Academic Press, 1989, pp. 227–246.
Metcalf, D., 1970, *J. Cell. Physiol.* 76:89–100.
Das, S. K. et al., 1981, *Blood* 58:630–641.
Das, S. K. et al., 1982, *J. Biol. Chem.* 257:13679–12681.
Stanley, E. R. et al., 1977, *J. Biol. Chem.* 252:4305–4312.
Wong, G. G. et al., 1987, *Science* 235:1504–1508.
Kawasaki, E. S. et al., 1985, *Science* 230:291–296.
Ladner, M. B. et al., 1987, *EMBO J.* 6:2693–2698.
Cerretti, D. P. et al., 1988, *Molecular Immunol.* 25:761–770.
Takahashi, M. et al., 1988, *Bioch. Biophs. Res. Comm.* 152:1401–1409.
Taniguchi, T. et al., 1983, *Nature* 302:305–110.
Devos et al., 1983, *Nucleic Acids Res.* 11:4307–4323.
Ceretti et al., 1986, *Proc. Natl. Acad. Sci. USA* 83:3223–3227.
*Chemical Abstracts*, 1987, 106:(21):170236f (abstract of Japanese Patent Publication No. 61/225199).

*Primary Examiner*—Marianne P. Allen
*Attorney, Agent, or Firm*—Philip L. McGarrigle; Donald Pochopian; Robert P. Blackburn

[57] ABSTRACT

Multifunctional proteins having M-CSF activity and at least one other bioactivity not found together in a single naturally occuring molecule are described. These multifunctional M-CSF proteins can be produced by the expression of fused genes which are also described. These multifunctional M-CSF proteins have increased therapeutic potential.

23 Claims, 1 Drawing Sheet

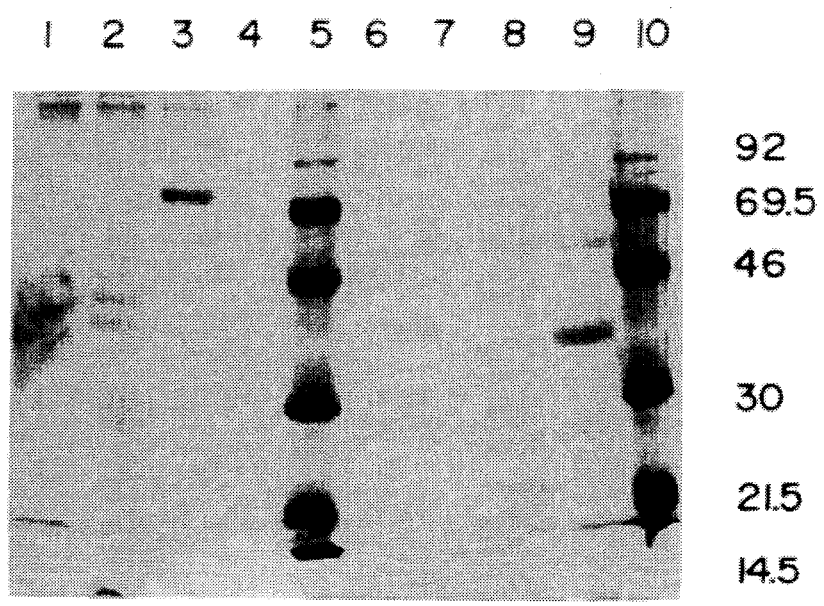
FIG._1.

MULTIFUNCTIONAL M-CSF PROTEINS AND GENES ENCODING THEREFOR

This is a continuation of U.S. application Ser. No. 07/995,338, filed Dec. 21, 1992, now abandoned, which is a continuation of U.S. application Ser. No. 07/340,228, filed Apr. 19, 1989, now abandoned.

BACKGROUND OF THE INVENTION

1. Field of the Invention

The present invention is in the field of biotechnology. More specifically, it relates to multifunctional proteins having two or more biological activities that are not found together in a single naturally occurring molecule. It further relates to the recombinant DNA that codes for M-CSF fusion proteins, the recombinant vectors that include the DNA, host organisms transformed with the recombinant vectors that produce the proteins, methods for producing the fusion proteins, pharmaceutical compositions containing the proteins and therapeutic methods employing the proteins.

2. Description of Related Disclosures

Recent technology has permitted the design of hybrid molecules which do not naturally occur. Fused selectable markers known as fusion flags to facilitate cloning, secretory leader peptide fusions to produce extracellular products and immunoconjugates are examples of such hybrid molecules. There have also been reports of attempts to produce hybrid proteins which possess potentially novel therapeutic properties by virtue of the combination of functions derived from each of the parent molecules. For example, hybrid interferons (IFNs) are disclosed in U.S. Pat. No. 4,758,428 and in European Patent Publication No. 0225579. Feng, G.-S. et al. (1988, *Science* 241:1501–1503) discloses a hybrid protein between IFN-γ and TNF-β which has increased antiproliferative activity in vitro compared with either IFN-γ or TNF-β alone. Japanese Patent Publication No. 61128889 discloses fusion proteins between IFN and urokinase. Hybrid plasminogen activators comprising, for example, fusions of urokinase and tissue plasminogen activator have also been reported. There are numerous disclosures of polypeptide-toxin hybrid proteins notwithstanding immunotoxins. For example, Kelley, V. E. et al. (1988, *Proc. Natl. Acad. Sci. USA* 85:3980–3984) report an IL-2/diphtheria toxin fusion protein which was found to be a potent immunosuppressive agent. U.S. Pat. No. 4,545,985 discloses IL-2/Pseudomonas exotoxin fusion proteins.

Another IL-2 fusion protein is disclosed in Australian Patent Abstract AU-A-66756/86 and European Patent Publication No. 0288809 (corresponding to PCT Patent Publication No. WO 87/02060) which report fusion proteins consisting of IL-2 and GM-CSF. The IL-2 sequence can be at either the N- or C-terminal end of the GM-CSF such that after acid cleavage of the fusion protein, GM-CSF having either N- or C-terminal sequence modifications can be generated.

In contrast, the present invention provides for the production of multifunctional proteins comprising M-CSF bioactivity produced by chemical or genetic fusion. Thus, the invention provides for the production of dimeric fusion proteins. It is surprising that these complex multifunctional homodimeric and heterodimeric proteins can be produced having two or more bioactivities since the refolding of M-CSF protein alone into its bioactive form is a complicated process. Furthermore, the multifunctional fusion proteins of the invention have increased therapeutic potential due to their multifunctional nature and their increased circulating half-life.

SUMMARY OF THE INVENTION

The present invention relates to DNA sequences encoding novel multifunctional proteins having two or more bioactivities not found together in a single naturally occurring molecule. The present invention further relates to a DNA sequence encoding a multifunctional fusion protein wherein one function of said protein in it active form is to stimulate the formation of primarily macrophage colonies in the in vitro colony stimulating assay of Ralph, P. et al., 1986, *Blood* 68:633. Since, M-CSF is active in its dimeric form, the invention relates to DNA sequences encoding multifunctional fusion proteins that are dimers. Further, the invention relates to DNA sequences encoding fusion proteins having M-CSF bioactivity and a second bioactivity associated with a protein selected from the group consisting of IL-1, IL-2, IL-3, IL-4, IL-5, IL-6, IL-7, α-IFN, β-IFN, γ-IFN, G-CSF, GM-CSF, TNF-α, TNF-β, erythropoietin (EPO), thrombopoietin or other platelet enhancing factors, ricin A, diphtheria toxin and Pseudomonas exotoxin. The invention also relates to DNA sequences having the M-CSF bioactivity i.e., the function of stimulating the formation of primarily macrophage colonies in the in vitro assay, encoded 5' to the second bioactivity. Among other surprising results, the present invention provides DNA sequences that encode for M-CSF/IL-2 fusion monomers that associate into dimers having both M-CSF and IL-2 bioactivities and that have the potential for a longer half-life due to the larger molecular size of the fused molecule.

Furthermore, the present invention relates to DNA sequences encoding for a multifunctional fusion protein including an amino acid sequence substantially equivalent to the amino acid sequence of M-CSF. The invention further relates to DNA sequences encoding the amino acid sequence of M-CSF which additionally encode the amino acid sequence substantially equivalent to the amino acid sequence of IL-2, IL-1α, IL-1β, IFN-γ, G-CSF or IL-6. The invention also relates to DNA sequences comprising coding sequence from a second protein in addition to M-CSF which hybridize under stringent conditions to the DNA encoding an amino acid sequence substantially equivalent to that of M-CSF or its complementary strand. DNA sequences comprising coding sequence from IL-2, IL-1α, IL-1β, IFN-γ, G-CSF or IL-6 in addition to M-CSF which hybridize under stringent conditions to the fused genes are embodiments of the present invention as well. The cell cultures transformed with the DNAs described and the expression systems comprising the DNAs described are also among the embodiments of the present invention.

Additionally, the present invention relates to novel multifunctional proteins wherein one function of the protein in its active form is to stimulate the formation of primarily macrophage colonies in the in vitro colony stimulating assay of Ralph, P. et al., (supra). The invention further relates to multifunctional proteins which are fusion proteins and which are dimers. Additionally, the invention relates to mulifunctional proteins comprising M-CSF activity and a second bioactivity associated with a protein selected from the group consisting of IL-1, IL-2, IL-3, IL-4, IL-5, IL-6, IL-7, α-IFN, β-IFN, γ-IFN, G-CSF, GM-CSF, TNF-α, TNF-β, EPO, thrombopoietin or other platelet enhancing factors, ricin A, diptheria toxin and Pseudomonas exotoxin. The invention further relates to multifunctional proteins wherein the function of stimulating the formation of primarily macrophage colonies in the in vitro assay resides in the amino-terminal end of the molecule. Also included in the invention are multifunctional proteins whch are heterodimers comprising monomeric subunits each having different second bioactivity associated with a protein selected from the group consisting of IL-1, IL-2, IL-3, IL-4, IL-5, IL-6, IL-7, α-IFN, β-IFN, γ-IFN, G-CSF, GM-CSF, TNF-α, TNF-β, EPO, thrombopoietin or other platelet enhancing factors, ricin A, diptheria toxin and Pseudomonas exotoxin.

BRIEF DESCRIPTION OF THE DRAWINGS

FIG. 1 shows immunoaffinity purified multifunctional fusion products encoded by PmL1 separated by SDS-PAGE and stained with Coomassie blue.

MODES OF CARRYING OUT THE INVENTION

A. Definitions

As used herein, the term "multifunctional M-CSF proteins" refers to proteins having the ability to stimulate the formation of primarily macrophage colonies in the in vitro colony stimulating assay of Ralph, P. et al., supra and at least one other biological activity which are conjugated either chemically or genetically and which are not found together in a single naturally occurring molecule. Hybrid genes which encode for these multifunctional M-CSF fusion proteins are produced by recombinant DNA technology. The multifunctional fusion proteins disclosed herein have macrophage colony stimulating factor activity as described below as one of their bioactivities. This M-CSF bioactivity may result from the M-CSF coding sequence at either the amino-terminal or carboxy-terminal end of the hybrid gene. Additionally, since native M-CSF is a dimer, the multifunctional fusion proteins of the invention as disclosed herein occur as dimeric or higher multimeric fusion proteins. Each monomeric subunit of these dimeric fusion proteins may have a second bioactivity. In the case of heterodimeric fusion proteins, only one subunit may have a second bioactivity or, in the alternative, each subunit may have a different second bioactivity resulting, in fact, in a trifunctional heterodimeric M-CSF fusion protein.

In addition to the combination of activities genetically, it should be clear that the hybrid proteins disclosed herein can be made by chemically conjugating portions of the M-CSF protein with the second bioactive protein. Examples of chemical conjugation are shown in U.S. Pat. Nos. 4,468,382 and 4,545,985, in Pirker et al., 1985, J. Clin. Invest. 76:1261–1267, Veronese, et al., 1985, *Biochem. & Biotech.* 11:141–152 and in commonly owned U.S. Ser. No. 146,275 each of which is incorporated herein by reference in its entirety. Since native M-CSF is a dimer, the conjugated multifunctional proteins of the invention can occur as dimeric or higher multimeric proteins. Each M-CSF monomer of the multifunctional proteins may be conjugated to a second bioactivity. In the case of heterodimeric conjugates, chemical coupling is carried out with monomeric M-CSF followed by refolding a mixture of differentially conjugated M-CSF monomers into active forms. Alternatively, by using an intact (refolded) M-CSF protein which has different monomeric subunits, each monomer can be selectively conjugated to different second bioactive proteins. Only one M-CSF subunit may have a second bioactivity or, in the alternative, each subunit may have a different second bioactivity resulting, in fact, in a trifunctional heterodimeric M-CSF protein. The M-CSF conjugates envisioned may have a more complex multimeric structure dependent upon the nature of the protein having the second bioactivity, eg. antibodies.

M-CSF can be coupled to toxin molecules including diphtheria toxin, ricin A toxin or Pseudomonas exotoxin from which the cell-recognition portion of the toxin molecule has been removed. Such multifunctional CSF-toxin conjugates are useful in the treatment of myeloid leukemia, autoimmune diseases, inflammation, graft rejection or other diseases when the target cells express M-CSF receptors. M-CSF can also be fused to blood proteins which target bone marrow blood cell precursors including IL-1, IL-3, IL-6, GM-CSF and G-CSF. M-CSF can be coupled to antibodies that result in similar localization to bone marrow blood cell precursors. Preferably the proteins appropriate for the multifunctional proteins described herein include IL-1, IL-2, IL-3, IL-4, IL-5, IL-6, IL-7, α-IFN, β-IFN, γ-IFN, G-CSF, GM-CSF, TNF-α, TNF-β, EPO, thrombopoietin or other platelet enhancing factors, ricin A, diptheria toxin and Pseudomonas exotoxin. EPO, thrombopoietin or other platelet enhancing factors, ricin A, diphtheria toxin and Pseudomonas exotoxin. Most preferably the proteins appropriate for the fusions described herein are M-CSF, IL-2, IL-1, IL-6, G-CSF and IFN-γ. The interactions of some of these factors has been recently reviewed (Ralph, P. et al., in *The Year In Immunology* 1988, Cruse et al., eds., Basel, Karger, 1989, Vol. 5, pp. 103–125; Ralph, P., "Colony Stimulating Factors" in *Human Monocytes* Asherson et al., eds. Academic Press, 1989, pp. 227–246).

As used herein, the term "M-CSF" refers to recombinant macrophage colony stimulating factor or macrophage colony stimulating factor-like proteins produced by a transformed host cell whose amino acid sequence is the same as, similar to, or substantially equivalent to the unglycosylated and/or glycosylated native macrophage colony stimulating factor. Substantially equivalent means the sequences are identical or differ by one or more amino acid alterations (deletions, additions or substitutions) that do not cause an adverse functional dissimilarity in biological activity between the synthetic and native protein. M-CSF is a protein which exhibits the spectrum of activity understood in the art for M-CSF-also known as CSF-1 i.e., when applied to the standard in vitro colony stimulating assay of Metcalf, D., *J. Cell. Physiol.* (1970) 76:89 as modified by Ralph, P. et al., supra, it is capable of stimulating the formation of primarily macrophage colonies. Native M-CSF is a glycosylated dimer, dimerization is reported to be necessary for activity as the monomer is not active in the Metcalf or Ralph colony stimulating assays (supra) or various other in vitro bioactivity assays (Das, S. K. et al., 1981, *Blood* 58:630–641; Das, S. K. et al., 1982, *J. Biol. Chem.* 257:13679–13681; Stanley, E. R. et al., 1977, *J. Biol. Chem,* 252:4305–4312, Halenbeck, R. et al., 1989, Bio/Technology in press). It should be noted that a low level of activity was observed in the assay of a monomer used by Halenbeck et al. supra but this was due to dimerization of M-CSF during the assay. The monomeric form may be converted to the dimeric form by in vitro provision of suitable refolding conditions, and the monomer is per se useful as an antigen to produce anti-M-CSF antibodies.

There appears to be some species specificity: Human M-CSF is operative both on human and on murine bone marrow cells; murine M-CSF does not show activity with human cells. Therefore, "human" M-CSF should be positive in the specific murine radioreceptor assay of Das et al., 1981, (supra), although there is not necessarily a complete correlation. The biological activity of the M-CSF protein will generally also be inhibited by neutralizing antiserum to human urinary M-CSF (Das, S. K. et al., 1981, supra). However, in certain special circumstances this criterion may not be met. For example, a particular antibody preparation may recognize a M-CSF epitope not essential for biological function, and which epitope is not present in the particular M-CSF mutein being tested or which is obscured by the tertiary structure of the M-CSF fusion protein. For purposes of definition herein, the M-CSF must (1) stimulate the formation of monocyte-macrophage colonies using bone marrow cells from the appropriate species as starting materials, (2) under most circumstances (see above) show inhibition of this activity by neutralizing antiserum against purified human urinary M-CSF, and(3) where appropriate for species type, exhibit a positive response to the radioreceptor assay.

M-CSF apparently occurs in numerous forms all which are included in the embodiments of the present invention. Human M-CSF cDNA clones coding for M-CSF proteins of three different lengths (α, 256 amino acids; β, 554 amino acids; and γ, 438 amino acids) have been isolated from cells expressing the single M-CSF gene (Wong, et al., 1987, *Science* 235:1504–1508; Kawasaki, et al., 1985, *Science* 230:291–296; Ladner et al., 1987, *Embo J.* 6:2693–2698; Cerretti, D. P. et al., 1988, *Molecular Immunol.* 25:761–770). The M-CSF proteins useful in the multifunctional proteins disclosed herein may also be processed by proteolysis. It is believed that M-CSF may occur in nature in one or more C-terminally deleted forms. In addition, M-CSFs lacking the first two or four amino acids have been isolated in active form from the supernatant of the human cell line AGR-ON (equivalent to CEM-ON; ATCC No. CRL-8199; Takahashi, M. et al., 1988, *Bioch. Biophys. Res. Comm.* 152:1401–1409). M-CSF protein comprising monomers ending at amino acid 145 are reported to have in vitro biological activity (European Patent Publication No. 0261592 published Mar. 30, 1988 incorporated herein by reference in its entirety). The monomeric M-CSF polypeptide (whether clipped at the C-terminus or not) may also refold to form multimers, most frequently dimers.

Thus, a protein including an amino acid sequence substantially equivalent to the amino acid sequence of M-CSF comprising: Glu-Tyr-Cys-Ser-His-Met-Ile-Gly-Ser-Gly-His-Leu-Gln-Ser-Leu-Gln-Arg-Leu-Ile-Asp-Ser-Gln-Met-Glu-Thr-Ser-Cys-Gln-Ile-Thr-Phe-Glu-Phe-Val-Asp-Gln-Glu-Gln-Leu-Lys-Asp-pro-Val- Cys-Tyr-Leu-Lys-Lys-Ala-Phe-Leu-Leu-Val-Gln-Asp-Ile-Met-Glu-Asp-Thr-Met-Arg-Phe-Arg-Asp-Asn-Thr-Pro-Asn-Ala-Ile-Ala-Ile-Val-Gln-Leu-Gln-Glu-Leu-Ser-Leu- Arg-Leu-Lys-Ser-Cys-Phe-Thr-Lys-Asp-Tyr-Glu-Glu-His-Asp-Lys-Ala-Cys-Val-Arg- Thr-Phe-Tyr-Glu-Thr-Pro-Leu-Gln-Leu-Leu-Glu-Lys-Val-Lys-Asn-Val-Phe-Asn-Glu- Thr-Lys-Asn-Leu-Leu-Asp-Lys-Asp-Trp-Asn-Ile-Phe-Ser-Lys-Asn-Cys-Asn-Asn-Ser- Phe-Ala-Glu and the DNA sequence encoding therefor are considered to be within the scope of the instant invention.

Native human urinary M-CSF has been isolated as a highly glycosylated dimer of 45–90 kd, depending on the source, method of measurement and identity of the reporter. The recombinantly produced unglycosylated M-CSF reported by Wong, G. G. et al., supra, appears to have a subunit molecular weight of approximately 21 kd. On the other hand, the molecular weight calculated on the basis of the amino acid sequence deduced for the "short" 224 amino acid form of M-CSF (SCSF) by Kawasaki, E. S. et al. (supra) (also U.S. Ser. No. 157,094 and PCT Patent Publication No. WO 86/04607 published Aug. 14, 1986 each of which is incorporated herein by reference in its entirety) is on the order of 26 kd, while that of the "long" 522 amino acid form (LCSF) is calculated to be on the order to 55 kd (Wong, G. G. et al. (supra); Ladner, M. B. et al. (supra); commonly owned U.S. Ser. Nos. 039,654, now abandoned, 039,657 now abandoned and 105,261 now abandoned, corresponding European Patent Publication No. 0272779 published Jun. 29, 1988; and PCT Patent Publication No. WO 87/06954 published Nov. 19, 1987 each of which is incorporated herein by reference in its entirety). When deleted constructs of these genes are expressed in *E. coli* (where glycosylation does not occur), they, of course, give rise to proteins of considerably lower molecular weight. The amino acid sequence of SCSF and a DNA sequence encoding the same are provided herein as SEQ ID NO: 4 and SEQ ID NO: 3 respectively, and are the same as the sequences of FIG. 1 from either U.S. Ser. Nos. 07/039,654 or 07/039,657 above. The amino acid sequence encoding for LCSF and a DNA sequence encoding the same are provided in SEQ ID NO: 2 and SEQ ID NO: 1 respectively, and are the same as the sequences of FIG. 2 of U.S. Ser. Nos. 07/039,654 or 07/039, 657.

It is, of course, well known that bacterially produced mature proteins which are immediately preceded by an ATG start codon may or may not include the N-terminal methionine in the form as produced and recovered. In addition, slight modification of the N-terminal sequence may aid in the processing of the N-terminal methionine, and it is shown in commonly owned European publication No. 0272779, that deletion of residues 1 and 2 (both glutamic acid) or residues 1–3 (glu-glu-val) aids in this manner. Deletions are noted by a ∇ followed by the number of amino acids deleted from the N-terminal sequence, or by the number of amino acids remaining when residues are deleted from the C-terminal sequence. Thus, the N-terminal deletions referred to above having the first 2 and the first 3 residues deleted are designated N∇2 and N∇3, respectively. C-terminal truncations of M-CSF resulting in proteins of 150, 158, 190 or 221 amino acids in length for example are referred to as C∇150, C∇158, C∇190 and C∇221, respectively. A 221 amino acid M-CSF molecule derived from the long form LCSF having an N-terminal deletion of 3 amino acids is denoted by LCSF/N∇3 C∇221 for example. Amino acid substitutions are designated by reference to the position of the amino acid which is replaced. For example, substitution of the cysteine residue at position 157 in FIG. 4 of Ladner et al., (supra) by serine is referred to as M-CSF $ser_{157}$. Accordingly, all of these forms may be used in the fusion proteins produced by the process disclosed herein.

In summary, in addition to the N-terminal and C-terminal deletions and aggregations, individual amino acid residues in the chain may be modified by oxidation, reduction, deletion or other derivatization, and these proteins may also be cleaved and/or polymerized to obtain products that retain activity. Such alterations which do not destroy activity do not remove the protein sequence from the definition, and are specifically included as substantial equivalents. M-CSF derived from other species may fit the definition of a protein having activity of "human M-CSF" by virtue of its display of the requisite pattern of activity as set forth above with regard to human substrate.

As used herein, the term "IL-2" refers to recombinant interleukin-2 or interleukin-2-like proteins produced by a transformed host cell and whose amino acid sequence is the same as or similar or substantially equivalent to the unglycosylated and/or glycosylated native human interleukin-2. Examples of such IL-2s are those described in European Patent Publication Nos. 091,539, 088,195, 109,748 and 200,280; those described in commonly owned U.S. Pat. Nos.

4,518,584 and 4,752,585 and in U.S. Pat. Nos. 4,738,927 and 4,778,879, each of which is incorporated herein by reference in its entirety; IL-2 described by Taniguchi et al., 1983, *Nature* 302:305–310 and Devos et al., 1983, *Nucleic Acids Res.* 11:4307–4323; and bovine IL-2 as described by Cerretti et al., 1986, *Proc. Natl. Acad. Sci USA* 83:3223–3227. The disclosures of all these references are incorporated herein by reference. The amino acid sequence of mature native IL-2, as disclosed in FIG. 1 of U.S. Pat. No. 4,752,585, has 133 amino acid residues and is provided as SEQ ID NO: 5 herein. The amino acid sequence of des-alanyl-IL-$2_{ser\ 125}$, as disclosed in FIG. 15b of U.S. Pat. No. 4,518,584, is provided herein as SEQ ID NO: 6.

The IL-2s preferred herein include biologically active muteins (analogs) of human IL-2 in which amino acid residues not essential to biologically activity have been deliberately deleted or replaced with a conservative amino acid as indicated below. The gene encoding des-alanyl-IL-$2_{cys\ 125}$ is available in pLW1 deposited as ATCC No. 39405. IL-2s preferred in the multifunctional proteins of the invention also include those wherein the cysteine residue at position 125 is replaced with another amino acid, preferably neutral or conservative, to eliminate sites for intermolecular crosslinking or incorrect intramolecular disulfide and, optionally, the N-terminal alanine residue of the native counterpart is eliminated. By a "conservative" amino acid substitution is meant one which does not change the activity characteristics of the protein, and in general is characterized by chemical similarity of the side chains of the two residues interchanged. for example, acidic residues are conservatively replaced by other acidic residues, basic by basic, hydrophobic by hydrophobic, bulky by bulky, and so forth. The degree of similarity required depends, of course, on the criticality of the amino acid for which substitution is made, and its nature. Thus, in general, preferred substitutions for cysteine residues are serine and alanine; for aspartic acid residues, glutamic acid; for lysine or arginine residues, histidine; for leucine residues, isoleucine, or valine; for tryptophan residues, phenylalanine or tyrosine; and so forth. More particularly, IL-2 muteins useful in the multifunctional proteins of this invention are those wherein (1) the cysteine residue at amino acid position 125 of the native counterpart is replaced by a serine residue (designated IL-$2_{ser\ 125}$; encoded in pLW55 deposited as ATCC No. 39516) or alanine residue (designated IL-$2_{ala125}$); or (2) the initial alanine residue is eliminated and the cysteine at position 125 is replaced by serine SEQ ID NO: 6 (designated des-alanyl-IL-$2_{ser125}$; encoded in pLW45 deposited as ATCC No. 39626).

Other IL-2s useful herein are those biologically active muteins described in U.S. Pat. No. 4,752,585 issued Jun. 21, 1988 (equivalent to European Patent Publication No. 200, 280 published Dec. 10, 1986) wherein oxidation-susceptible methionine residues are replaced with a neutral or conservative amino acid, a preferred mutein includes replacing the methionine at position 104 with a conservative amino acid such as alanine.

EPO 200,280 also describes amino-terminal deletions of IL-2 wherein one or more of the first six amino acids are deleted. Other amino-terminal deletions of IL-2 are disclosed in *Chemical Abstracts*, 1987, 106:(21 ):170236f, an abstract of Japanese Patent Publication No. 61/225,199 published October 1986, wherein any one of the first 15 amino acids of IL-2 are deleted. PCT Patent Publication No. WO 87/04714, published Aug. 13, 1987 describes deletions or replacements of one or more of the amino acid residues in positions 2 to 11 and/or 128 to 133 from the amino-terminal alanine of IL-2. Thus, a multifunctional M-CSF protein including an amino acid sequence substantially equivalent to the amino acid sequence of IL-2 comprising: Thr-Lys-Lys-Thr-Gln-Leu-Gln-Leu-Glu-His-Leu-Leu-Leu-Asp-Leu-Gln-Met-Ile-Leu- Asn-Gly-Ile-Asn-Asn-Tyr-Lys-Asn-Pro-Lys-Leu-Thr-Arg-Met-Leu-Thr-Phe-Lys-Phe- Tyr-Met-Pro-Lys-Lys-Ala-Thr-Glu-Leu-Lys-His-Leu-Gln-Cys-Leu-Glu-Glu-Glu-Leu- Lys-Pro-Leu-Glu-Glu-Val-Leu-Asn-Leu-Ala-Gln-Ser-Lys-Asn-Phe-His-Leu-Arg-Pro-Arg-Asp-Leu-Ile-Ser-Asn-Ile-Asn-Val-Ile-Val-Leu-Glu-Leu-Lys-Gly-Ser-Glu-Thr-Thr-Phe-Met-Cys-Glu-Tyr-Ala-Asp-Glu-Thr-Ala-Thr-Ile-Val-Glu-Phe-Leu-Asn-Arg-Trp- Ile-Thr-Phe-Cys-Gln-Ser-Ile-Ile-Ser-Thr-Leu-Thr and DNA sequences encoding therefor are considered to be within the scope of the instant invention.

As used herein the term "IFN-γ" refers to recombinant interferon-gamma or interferon-gamma-like proteins produced by a transformed host cell and whose amino acid sequence is the same as or substantially equivalent to the unglycosylated and/or glycosylated native human or murine interferon-gamma. The IFN-γs preferred herein are those biologically active, essentially full-length forms, of IFN-γ. Human IFN-γ and derivatives thereof have been described in U.S. Pat. No. 4,762,791 issued Aug. 9, 1988 and incorporated herein by reference in its entirety. Human IFN-γ beginning with the 6th amino acid, Pro, and ending at the 127th amino acid, Ala, are reported to be active (European Patent Publication No. 219,781, published Apr. 29, 1987 and incorporated herein by reference in its entirety). Thus, a multifunctional M-CSF protein including an amino acid sequence substantially equivalent to the amino acid sequence of human IFN-γ comprising: Pro-Tyr-Val-Lys-Glu-Ala-Glu-Asn-Leu-Lys-Lys-Tyr-Phe-Asn-Ala-Gly-His-Ser-Asp-Val-Ala-Asp-Asn- Gly-Thr-Leu-Phe-Leu-Gly-Ile-Leu-Lys-Asn-Trp-Lys-Glu-Glu-Ser-Asp-Arg-Lys-Ile- Met-Gln-Ser-Gln-Ile-Val-Ser-Phe-Tyr-Phe-Lys-Leu-Phe-Lys-Asn-Phe-Lys-Asp-Asp- Gln-Ser-Ile-Gln-Lys-Ser-Val-Glu-Thr-Ile-Lys-Glu-Asp-Met-Asn-Val-Lys-Phe-Phe- Asn-Ser-Asn-Lys-Lys-Lys-Arg-Asp-Asp-Phe-Glu-Lys-Leu-Thr-Asn-Tyr-Ser-Val-Thr- Asp-Leu-Asn-Val-Gln-Arg-Lys-Ala-Ile-His-Glu-Leu-Ile-Gln-Val-Met-Ala-Glu-Leu- Ser-Pro-Ala-Ala (SEQ ID NO. 9) and DNA sequences encoding therefor are considered to be within the scope of the instant invention.

Murine IFN-γ and derivatives thereof have been described in Gray, P. W. et al., (1983, *Proc. Natl. Acad. Sci. USA* 80:5842–5846) and are used herein because IFN-γ is species specific. This is, human IFN-γ is not active in an assay using a murine cell line. Proteins having these amino acid sequences or substantially equivalent sequences which result in a proteins having the bioactivity understood in the art for IFN-γ are considered to be within the scope of the invention. Thus, a multifunctional M-CSF protein including an amino acid sequence substantially equivalent to the amino acid sequence of murine IFN-γ comprising: Cys-Tyr-Cys-His- Gly-Thr-Val-Ile-Glu-Ser- Leu-Glu-Ser-Leu-Asn-Asn-Tyr-Phe-Asn-Ser-Ser-Gly-Ile- Asp-Val-Glu-Glu-Lys-Ser-Leu-Phe-Leu-Asp-Ile-Trp-Arg-Asn-Trp-Gln-Lys-Asp-Gly- Asp-Met-Lys-Ile-Leu-Gln-Ser-Gln-Ile-Ile-Ser-Phe-Tyr-Leu-Arg-Leu-Phe-Glu-Val-Leu- Lys-Asp-Asn-Gln-Ala-Ile-Ser-Asn-Asn-Ile-Ser-Val-Ile-Glu-Ser-His-Leu-Ile-Thr-Thr- Phe-Phe-Ser-Asn-Ser-Lys-Ala-Lys-Lys-Asp-Ala-Phe-Met-Ser-Ile-Ala-Lys-Phe-Glu- Val-Asn-Asn-Pro-Gln-Val-Gln-Arg-Gln-Ala-Phe-Asn-Glu-Leu-Ile-Arg-Val-Val- His- Gln-Leu-Leu-Pro-Glu-Ser-Ser-Leu-Arg-Lys-Arg-Lys-Arg-Ser-Arg-Cys and DNA sequences encoding therefor are considered to be within the scope of the instant invention.

"G-CSF" as used herein refers to a recombinant protein having the effect of stimulating the production of primarily neutrophil colonies or neutrophil-macrophage colonies in a colony forming assay using bone marrow cell progenitors of an appropriate species. A protein having this activity and whose amino acid sequence is the same as or similar or substantially equivalent to unglycosylated and/or glycosylated native human G-CSF as disclosed in European Patent Publication No. 256,843, published Feb. 24, 1988 or U.S. Pat. No. 4,810,643 issued Mar. 7, 1989, incorporated herein by reference in its entirety, is considered to be within the scope of the invention. Thus, a multifunctional M-CSF protein including an amino acid sequence substantially equivalent to the amino acid sequence of G-CSF comprising: Pro-Leu-Gly-Pro-Ala-Ser-Ser-Leu-Pro-Gln-Ser-Phe- Leu-Leu-Lys-Cys-Leu-Glu-Gln- Val-Arg-Lys-Ile-Gln-Gly-Asp-Gly-Ala-Ala-Leu-Gln-Glu-Lys-Leu-Cys-Ala-Thr-Tyr-Lys-Leu-Cys-His-Pro-Glu-Glu-Leu-Val-Leu-Leu-Gly-His-Ser-Leu-Gly-Ile-Pro-Trp- Ala-Pro-Leu-Ser-Ser-Cys-Pro-Ser-Gln-Ala-Leu-Gln-Leu-Ala-Gly-Cys-Leu-Ser-Gln- Leu-His-Ser-Gly-Leu-Phe-Leu-Tyr-Gln-Gly-Leu-Leu-Gln-Ala-Leu-Glu-Gly-Ile-Ser- Pro-Glu-Leu-Gly-Pro-Thr-Leu-Asp-Thr-Leu-Gln-Leu-Asp-Val-Ala-Asp-Phe-Ala-Thr- Thr-Ile-Trp-Gln-Gln-Met-Glu-Glu-Leu-Gly-Met-Ala-Pro- Ala-Leu-Gln-Pro-Thr-Gln- Gly-Ala-Met-Pro- Ala-Phe-Ala-Ser-Ala-Phe-Gln-Arg-Arg-Ala-Gly-Gly-Val-Leu-Val- Ala-Ser-His-Leu-Gln-Ser-Phe-Leu-Glu-Val-Ser-Tyr-Arg-Val-Leu-Arg-His-Leu-Ala- Gln-Pro (SEQ ID NO: 7) and DNA sequences encoding therefor are considered to be within the scope of the instant invention.

As used herein, the term "IL-1" refers to recombinant interleukin-1 or interleukin-1-like proteins produced by a transformed host cell and whose amino acid sequence is the same as or substantially equivalent to the unglycosylated and/or glycosylated native human interleukin-1. Human interleukin-1 has been described in U.S. Pat. No. 4,801,686 issued Jan. 31, 1989, in European Patent Publication No. 165654 published Dec. 27, 1985, in PCT Patent Publication No. WO 85/00830 published Feb. 28, 1985, and in European Patent Publication No. 267629 published May 18, 1988 each incorporated herein by reference in its entirety. DNAs encoding for IL-1 have been described in European Patent Publication Nos. 188864 published Jul. 30, 1986 and 200986 published Nov. 12, 1986, European Patent Publication No. 259160 published Mar. 9, 1988 each incorporated herein by reference in its entirety. In addition, two forms of the IL-1 polypeptide, referred to as IL-1alpha (IL-1α) and IL-1beta (IL-1β), have been described (human IL-1α in March, C. J. et al., 1985, *Nature* 315:641 and human IL-1β in Auron, P. E. et al., 1984, *Proc. Natl. Acad. Sci. USA* 81:7907)). Both forms are considered in the definition of IL-1 as used herein. Thus, a multifunctional M-CSF protein including an amino acid sequence substantially equivalent to the amino acid sequence of IL-1α comprising: Met-Arg-Ile-Ile-Lys-Tyr-Glu-Phe-Ile-Leu-Asn-Asp-Ala-Leu-Asn-Gln- Ser-Ile-Ile-Arg-Ala- Asn-Asp-Gln-Tyr-Leu-Thr-Ala-Ala-Ala-Leu-His-Asn-Leu-Asp-Glu-Ala-Val-Lys-Phe- Asp-Met-Gly-Ala- Tyr- Lys-Ser-Ser-Lys- Asp-Asp-Ala-Lys-Ile-Thr-V al-Ile-Leu-Arg-Ile- Ser-Lys-Thr-Gln-Leu-Tyr-Val-Thr-Ala-Gln-Asp-Glu-Asp-Gln-Pro-Val-Leu-Leu-Lys- Glu-Met- Pro-Glu-Ile-Pro-Lys-Thr-Ile-Thr-Gly-Ser-Glu-Thr-Asn-Leu-Leu-Phe-Phe- Trp-Glu-Thr-His-Gly-Thr-Lys-Asn-Tyr-Phe-Thr-Ser-Val-Ala-His-Pro-Asn-Leu-Phe- Ile-Ala-Thr-Lys-Gln-Asp-Tyr-Trp-Val-Cys-Leu-Ala-Gly-Gly-Pro-Pro-Ser-Ile-Thr-Asp- Phe-Gln-Ile-Leu and DNA sequences encoding therefor are considered to be within the scope of the instant invention.

Similarly, a multifunctional M-CSF protein including an amino acid sequence substantially equivalent to the amino acid sequence of IL-1β comprising: Arg- Ser-Leu-Asn-Cys-Thr-Leu-Arg-Asp-Ser-Gln-Gln-Lys-Ser-Leu-Val-Met-Ser-Gly-Pro- Tyr-Glu-Leu-Lys-Ala-Leu-His-Leu-Gln-Gly-Gln-Asp-Met-Glu-Gln-Gln-Val-Val-Phe- Ser-Met-Ser-Phe-Val-Gln-Gly-Glu-Glu-Ser-Asn-Asp-Lys-Ile-Pro-Val-Ala-Leu-Gly- Leu-Lys-Glu-Lys-Asn-Leu-Tyr-Leu-Ser-Cys-Val-Leu-Lys-Asp-Asp-Lys-Pro-Thr-Leu- Gln-Leu-Glu-Ser-Val-Asp-Pro-Lys-Asn-Tyr-Pro-Lys-Lys-Lys-Met-Glu-Lys-Arg-Phe-Val-Phe-Asn-Lys-Ile-Glu-Ile-Asn-Asn-Lys-Leu-Glu-Phe-Glu-Ser- Ala-Gln-Phe-Pro- Asn-Trp-Tyr-Ile-Ser-Thr-Ser-Gln-Ala-Glu-Asn-Met-Pro-Val-Phe-Leu-Gly-Gly-Thr- Lys-Gly-Gly-Gln-Asp-Ile-Thr-Asp-Phe-Thr-Met-Gln-Phe (SEQ ID NO: 8) and DNA sequences encoding therefor are considered to be within the scope of the instant invention.

As used herein, the term "IL-6" refers to recombinant interleukin-6 or interleukin-6-like proteins produced by a transformed host cell and whose amino acid sequence is the same as or substantially equivalent to the unglycosylated and/or glycosylated native human interleukin-6. Human interleukin-6, also referred to as human B-cell differentiation factor, has been described by Hirano, T. et al. (1986, *Nature* 324:73–76, incorporated herein by reference in its entirety). Like IL-1, IL-6 affects very primitive hemopoietic cells and its multiple actions have been discussed in Wong, G. G., et al. (1988, *Immunol. Today* 9:137). Thus, a multifunctional M-CSF protein including an amino acid sequence substantially equivalent to the amino acid sequence of IL-6 comprising: Pro-Val-Pro-Pro-Gly-Glu-Asp-Ser-Lys-Asp-Val-Ala- Ala-Pro-His-Arg-Gln-Pro-Leu-Thr-Ser-Ser-Glu-Arg-Ile-Asp-Lys-Gln-Ile-Arg-Tyr-Ile-Leu-Asp-Gly-Ile-Ser-Ala-Leu-Arg-Lys-Glu-Thr-Cys-Asn-Lys-Ser-Asn-Met-Cys-Glu- Ser-Ser-Lys-Glu-Ala-Leu-Ala-Glu-Asn-Asn-Leu-Asn-Leu-Pro-Lys-Met-Ala-Glu-Lys- Asp-Gly-Cys-Phe-Gln-Ser-Gly-Phe-Asn-Glu-Glu-Thr-Cys-Leu-Val-Lys-Ile-Ile-Thr-Gly-Leu-Leu-Glu-Phe-Glu-Val-Tyr-Leu-Glu-Try-Leu-Gln-Asn-Arg-Phe-Glu-Ser-Ser- Glu-Glu-Gln-Ala-Arg-Ala-Val-Gln-Met-Ser-Thr-Lys-Val-Leu-Ile-Gln-Phe-Leu-Gln- Lys-Lys-Ala-Lys-Asn-Leu-Asp-Ala-Ile-Thr-Thr-Pro-Asp-Pro-Thr-Thr-Asn-Ala-Ser- Leu-Leu-Thr-Lys-Leu-Gln-Ala-Gln-Asn-Gln-Trp-Leu-Gln-Asp-Met-Thr-Thr-His-Leu- Ile-Leu-Arg-Ser-Phe-Lys-Glu-Phe-Leu-Gln-Ser-Ser-Leu-Arg-Ala-Leu-Arg-Gln-Met and DNA sequences encoding therefor are considered to be within the scope of the instant invention.

The precise chemical structure of the M-CSF, G-CSF, IL-2, IFN-γ IL- 6 or IL-1 protein depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, as well as by conjugation with saccharides, polyethylene glycols (PEGs) and polyoxyethylene glycols (POGs). Certain aspects of such augmentation are accomplished through post-translational processing systems of the producing host; other such modifications may be introduced in vitro. In any event, such modifications are included in the definition of protein herein so long as the activity of the protein, as defined above, is not destroyed. It is expected, of course, that such modifications may quantitatively or qualitatively affect the activity, either by enhancing or diminishing the activity of the protein in the various assays. Further, individual amino acid residues in the chain may be modified by oxidation, reduction or other derivatization, and the protein may be cleaved to obtain fragments which retain activity. Modification to the primary structure itself by deletion, addition or substitution of the amino acids incorporated into the sequence during translation can be made without destroying the activity of the protein. Such substitutions which do not destroy activity do not remove the protein sequence from the definition and are considered to have substantially equivalent amino acid sequences.

As used herein the term "transformed" in describing host cell cultures denotes a cell that has been genetically engineered to produce a heterologous protein that possesses the activity of the native protein. Examples of transformed cells are described in the examples of this application. Bacteria are preferred microorganisms for producing the protein. Synthetic protein may also be made by suitable transformed yeast and mammalian host cells.

The term "refractile material" designates material or bodies which refract light and appear as bright spots in microorganisms when viewed through a phase contrast microscope at magnifications as low as 1000 fold. Refractile material is also known as refractile or inclusion bodies. Examples of heterologous proteins which form refractile bodies in commonly found culture conditions include macrophage colony stimulating factor (M-CSF), interleukin-2 (IL-2), interferon-β (IFN-β), envelope protein from feline leukemia virus antigen (FeLV), human growth hormone (hGH), bovine growth hormone (bGH), and certain proteins coated or fused with a virus such as FMD virus. Certain proteins, such as interferon-alpha (IFN-alpha) and tumor necrosis factor (TNF), are more soluble in the cytoplasm.

"Operably linked" refers to juxtaposition such that the normal function of the components can be performed. Thus, a coding sequence "operably linked" to control sequences refers to a configuration wherein the coding sequence can be expressed under the control of these sequences.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell, are included. Where indistinct designations are intended, it will be clear from the context.

As used herein, the term "pharmaceutically acceptable" refers to a carrier medium which does not interfere with the effectiveness of the biological activity of the active ingredients and which is not toxic to the hosts to which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

As used herein, the term "prophylactic or therapeutic" treatment refers to administration to the host of the multifunctional M-CSF protein either before or after infection or cancer detection. If the multifunctional M-CSF protein is administered prior to exposure to the infecting agent, the treatment is prophylactic (i.e., it protects the host against infection), whereas if administered after infection or initiation of cancer, the treatment is therapeutic (i.e., it combats the existing infection or cancer).

As used herein the term "infectious disease" refers to any kind of infection including those caused by bacteria, fungi, viruses, protozoa or parasites. Examples of sources of bacterial infections include P. aeruginosa, E. coli, tetanus, Mycobacterium species, Streptococcal strains, Corynebacterium diphtheriae and Salmonella. Examples of sources of fungal infection include crypttococcosis, histoplasmosis, and other infections due to Candida species. Examples of viral infections include cytomegalovirus (CMV) Hepatitis A, recurrent Herpes Simplex 1 or 2, HIV I or II, Herpes Zoster, influenza, and rhinoviruses.

As used herein, the term "synergistic" refers to the effect of administering the multifunctional proteins disclosed herein being greater than the effect of administering the two or more bioactive components individually. This synergism can allow greater efficacy at an equal dose amount and thereby allow lower dosing resulting in reduced host toxicity.

As used herein, the term "stringent conditions" refers to conditions wherein hybridization is carried out at about 5° below the melting temperature ($T_m$) of the probe DNA in 5×SSC (standard saline citrate); 5×Denhardt's; 50 mM $NaPO_4$, pH 7; 5 mM EDTA; 0.1% SDS; and 200 μg/ml yeast RNA. The effective $T_m$ of the probe DNA can be lowered about 0.7° for every 1% formamide added. While the exact conditions vary with probe length, typical conditions for relatively long probes (e.g., more than 30–50 nucleotides) employ a temperature of 42°–55° C. and the above hybridization buffer containing about 20%–50% formamide. For shorter probes, lower temperatures of about 25°–42°, and lower formamide concentrations (0%–20%) are employed.

B. General Procedure

The multifunctional proteins of the invention offer an opportunity to link two or more functions in a single molecule which may act simultaneously on target cells. The dual signaling feature of these novel recombinant molecules may result in increased efficacy in the clinic. In addition, larger molecular size has been correlated to increased circulating half-life (Katre, N. et al., 1987, Proc. Natl. Acad. Sci. USA 84:1487–1491). The joining of two or more coding sequences having independent functions or bioactivities has the added advantage of creating a larger molecule with potential for a longer in vivo half-life resulting in increased efficacy.

The M-CSF proteins of the invention are capable both of stimulating monocyte-macrophage cell production from progenitor marrow cells, and of stimulating such functions of these differentiated cells as the secretion of lymphokines in the mature macrophages thus enhancing the effectiveness of the immune system. In general, any subject suffering from immunosuppression whether genetic or due to chemotherapy, bone marrow transplantation, or other, accidental forms of immunosuppression such as disease (e.g., acquired immune deficiency syndrome) would benefit from the availability of M-CSF for pharmacological use. In addition, subjects could be supplied systemically or locally with enhanced amounts of previously differentiated macrophages to supplement those of the indigenous system, which macrophages are produced by in vitro culture of bone marrow or other suitable preparations treated with M-CSF. These preparations include those of the patient's own blood monocytes, which can be so cultured and returned for local or systemic therapy. The ability of M-CSF to stimulate production of lymphokines by macrophages and to enhance their ability to kill target cells also makes M-CSF directly useful in treatment of neoplasms and infections.

Human IL-2 has a number of in vitro and in vivo effects including enhancing the proliferative responses of human peripheral blood mononuclear cells or murine thymocytes, enhancing the immune response in humans and in animals against bacterial, parasitic, fungal, protozoan and viral infections, and supporting the growth of continuous T cell lines. rIL-2 has been obtained form genetically engineered *E. coli* as an unglycosylated protein with biological activities equivalent to those of native, glycosylated IL-2. (Taniguchi et al., 1983, supra; Rosenberg, S. A. et al., 1984, *Science* 223:1412–1415; Wang, A. et al., 1984, *Science* 224:1431–1433; and Doyle, M. et al., 1985, *J. Biol. Resp. Modifiers* 4:96–109). Rosenberg and his coworkers have shown that systemic administration of rIL-2 in high doses causes regression of established metastatic cancers (Rosenberg et al., 1985, *J. Exp. Med.* 313:1485–1492; Rosenberg et al., 1986, *Science* 233:1318–1321).

The M-CSF/IL-2 multifunctional protein has synergistic effects compared to the use of either protein separately. This synergism allows greater efficacy at an equal dose amount and thus allows lower dosing resulting in reduced host toxicity. Pharmacokinetics show that the multifunctional protein increases half-life in the plasma when injected in an intravenous bolus compared to the half-life in the plasma of either drug administered separately.

The M-CSF/IL-2 multifunctional protein is tested for in vitro efficacy in cancer therapy and in infectious diseases. Both IL-2 and M-CSF administered individually show a dose-related inhibition of rumor growth in the subcutaneous METH A sarcoma model in BALB/c mice (see Katre, N. et al. supra for IL-2 and commonly owned U.S. Ser. No. 243,253 for M-CSF each incorporated herein by reference in its entirety). Both IL-2 and M-CSF proteins also demonstrate activity in the B16 melanoma model against metastases. The multifunctional protein also shows this dose-related inhibition of rumor growth, albeit at substantially lower doses and therefore with substantially reduced toxicity. The beneficial activity of the multifunctional protein is demonstrated in preclinical cancer models, e.g. murine B16 melanoma, in which IL-2 decreases the tumor load therapeutically, and M-CSF decreases the number and size of lung metastases when given prophylactically, for i.v. or s.c. injection of B16 cells as disclosed in PCT Patent Publication No. WO 89/02746 published Apr. 6, 1989 and incorporated herein by reference in its entirety.

M-CSF and IL-2 are each efficacious when administered independently in various infectious disease models. Bacterial and viral infections may be treated effectively with M-CSF and IL-2 administered individually. For example, M-CSF injections have been shown to protect mice from a lethal *E. coli* challenge (Chong et al., 1988, *FASEB. J.* 2(5):A1474) and to protect against fungal Candida infection (Chong, K. T. et al., presented at 1989 American Society for Microbiology Meeting, New Orleans, La.). Cytomegaloviral infection was less severe in M-CSF treated mice (U.S. application Ser. No. 243,253). M-CSF has been demonstrated to inhibit vesicular stomatitis virus (VSV) replication and cytopathology in mouse macrophages in vitro (Lee et al., 1987, *J. Immunol.* 138:3019–3022) IL-2 has also been shown to protect mice from a lethal challenge to Gram-negative bacteria such as *E. coli* and *Pseudomonas aeruginosa* (European Patent Publication No. 0242233 published Oct. 21, 1987) and to cure infected mice (Goronzy, J. et al., 1989, *J. Immunol* 142:1134–1138). 1L-2 has been shown to be useful in the treatment of recurrent herpes simplex virus in guinea pigs (Merigan et al., 1988, *J. Immunol.* 140:294–299). The M-CSF/IL-2 multifunctional protein is also effective in the treatment of bacterial, vital or fungal infections but at a substantially lower dose than either component alone, and therefore with substantially reduced toxicity.

The M-CSF/IL-1 multifunctional protein has synergistic effects compared to the use of either protein separately. M-CSF has been shown to act synergistically with IL-1 in vitro in promoting myeloid cell growth from mouse bone marrow cells (Moore, M. A. S., et al. *Recent Advances in Leukemia and Lymphoma*, Alan R. Liss, Inc., 445–456; Mochizuki, D. Y. et al., *Proc. Natl. Acad. Sci. USA* 84:5267–5271; Zsebo, K. M. et al., 1988, *Blood* 71:962–968). IL-1 has demonstrated synergism with other CSFs such as G-, GM- and multi-CSF or IL-3 for myelopoiesis in vitro (Bartelmez, S. H. et al., *Exp. Hematol.* 17:240–245). In addition, U.S. Pat. No. 4,808,611 issued Feb. 28, 1989 incorporated herein by reference in its entirety discloses a method of inducing proliferation and differentiation of hematopoietic stem cells in mammals by the administration of both IL-1 and a CSF. The M-CSF/IL-1 multifunctional protein is more effective than either agent alone, or than the combination of individual agents, at the same dose amounts because the half-lives of each activity in the circulation are increased and the activities are focussed in the bone marrow where they need to be located in order to be effective. For many of these same reasons, the M-CSF/IL-6 multifunctional protein is also useful. (See Bot, F. J. et al., 1989, *Blood*, 73:435–437)

The M-CSF/IFN-γ multifunctional protein also has synergistic effects compared to the use of either protein separately. Stimulation of mouse macrophages (Nakoinz, I. et al., 1988, *Cell. Immunol.* 116:331–340) and human monocytes (Sampson-Johannes et al., 1988, *J. Immunol* 114:3680–3686) with the combination of M-CSF and IFN-γ in vitro gave greater cytolytic activity against tumor cells than stimulation by either agent alone. Use of IFN-γ in cancer therapy in vivo has been limited by toxicity even though it is well known as a good stimulator of macrophage anti-tumor activity (Nakoinz et al., supra; Sampson-Johannes et al., supra). A M-CSF/IFN-γ multifunctional protein is ideal for both delivering these macrophage effector cells to the target tumors and for activating their cytolytic capacity. Data has indicated that IFN-γ synergizes with M-CSF when administered concurrently (Nakionz, I. et al., supra). The multifunctional protein which embodies both activities has a longer half-life in the circulation and serves to direct more of the IFN-γ onto the macrophages, leading to increased efficacy and less toxicity to other cell types.

Similar efficacy for the M-CSF/IFN-γ multifunctional protein is seen in infectious diseases. M-CSF injections protect mice from lethal in Vitro challenge (Chong, et al., supra). M-CSF inhibits vesicular stomatosis virus replication and cytopathology in mouse macrophages in vitro (Lee et al., supra). M-CSF stimulates mouse macrophages to kill intracellular Candida in vitro (Karbassi, A. et al., 1987, *J. Immunol.* 139:417–421 ). A number of investigators have shown that IFN-γ stimulates macrophages in vitro to kill or resist infection by a variety of microbial metazoan pathogens. The M-CSF/IFN-γ multifunctional protein is shown to be more efficacious than either protein separately, or separate molecules when mixed together, at the same dose, when tested in these models in vitro or in vivo.

The M-CSF/G-CSF multifunctional protein provides a means to augment the effect of either CSF-1 and G-CSF administered individually by combining them in therapeutic use. The use of these two factors is synergistic with respect to eliciting enhancement of the immune system. (See Tsuneoka, K. et al., 1984, *Cell Structure and Function,* 9:67–81 and Metcalf, D. et al., 1985, *Leukemia Res.,* 9:35–50) Together their effect is greater than the sum obtained from simple addition of the effect of either acting alone. It is therefore possible to achieve the desired effect using smaller amounts of the multifunctional protein than would be required by administration of the individual proteins, thus offering the opportunity to reduce side effects and any toxicity which might be associated with elevated doses.

For parenteral administration the multifunctional proteins of the invention will generally be formulated in a unit dosage injectable form (solution, suspension, emulsion), preferably in a pharmaceutically acceptable carrier medium which is inherently non-toxic and non-therapeutic or non-prophylactic. Examples of such vehicles include saline, Ringer's solution, dextrose solution, mannitol, and normal serum albumin.

1. Vector Construction

Construction of suitable vectors containing the desired coding and control sequences employs standard ligation and restriction techniques which are well understood in the art (e.g., Maniatis et al., Molecular Cloning: A Laboratory Manual, Cold Spring Harbor Laboratory, 1982; Ausubel, F. M. et al., eds. *Current Protocols in Molecular Biology,* Greene Publishing Assoc., New York). Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology,* 1980, 65:499–560.

Restriction-cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 μM dNTPs. The Klenow fragment fills in at 5' sticky ends but chews back protruding 3' single strands, even though the four dNTP are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared by the triester method of Matteucci, et al., 1981, *J. Am. Chem. Soc.* 103:3185–3191 of using automated synthesis methods. Kinasing of single strands prior to annealing or for labeling is achieved using an excess, e.g., approximately 10 units of polynucleotide kinase to 1 nmole substrate in the presence of 50 mM Tris, pH 7.6, 10 mM MgCl$_2$, 5 mM dithiothreitol, 1–2 mM ATP. If kinasing is for labeling of probe, the ATP will contain high specific activity γ-$^{32}$p.

Ligations are performed in 15–30 μl volumes under the following standard conditions and temperature: 20 mM Tris-Cl pH 7.5, 10 mM MgCl$_2$, 10 mM DTT, 33 μg/ml BSA, 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100-nM total end concentration). Intermolecular blunt end ligations (usually employing a 10–30 fold molar excess of linkers) are performed at 1 μM total ends concentration. Intermolecular blunt end ligations (usually employing a 10–30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per μg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

2. Cloning by Polymerase Chain Reaction (PCR)

A specific nucleic acid sequence may be cloned into a vector by using primers to amplify the sequence which contain restriction sites on their non-complementary ends according to the general methods as disclosed in U.S. Pat. Nos. 4,683,195 issued Jul. 28, 1987, 4,683,202 issued Jul. 28, 1987 and 4,800,159 issued Jan. 24, 1989 the latter of which is incorporated herein by reference in its entirety. A modification of this procedure involving the use of the heat stable *Thermus aquaticus* (Taq) DNA polymerase has been described in commonly owned copending application U.S. Ser. No. 063,647, filed Jun. 17, 1987 now U.S. Pat. No. 4,965,188 incorporated herein by reference in its entirety. The Taq polymerase used in this method has been further characterized in European Patent Publication No. 258017 published Mar. 2, 1988 incorporated herein by reference in its entirety. Also useful is the Thermal Cycler instrument (Perkin-Elmer-Cetus) which has been described in commonly owned copending application U.S. Ser. No. 899,061 filed Aug. 22, 1986 now abandoned also incorporated herein by reference in its entirety.

Generally, the nucleic acid sequence to be cloned is treated with one oligonucleotide primer for each strand and an extension product of each primer is synthesized which is complementary to each nucleic acid strand. An alternative to the use of plasmid DNAs encoding the lymphokines of interest as template for PCR is the use of RNA from any cell producing these lymphokines as template for PCR as described in U.S. Pat. No. 4,800,159. If RNA is the available starting material, the extension product synthesized from one primer when separated from its complement can serve as template for synthesized of the extension product of the other primer. As previously mentioned, each primer contains a restriction site on its 5' end which is the same as or different from the restriction site on the other primer. After sufficient amplification has occurred the amplification products are treated with the appropriate restriction enzyme(s) to obtain cleaved products in a restriction digest. The desired fragment to be cloned is then isolated and ligated into the appropriate cloning vector.

3. Modification of DNA Sequences

For portions of vectors derived from cDNA or genomic DNA which require sequence modifications, site-specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature which permits hybridization of an exact match, but at which the mismatches with the original strand are sufficient to prevent hybridization. Plaques which hybridize with the probe are then picked and cultured, and the DNA is recovered. Details of site specific mutation procedures are described below in specific examples.

For example, pCSF-BamBcl contains the entire M-CSF encoding sequence except that the serine at position 159 is mutated to a stop codon. To accomplish this, the coding sequence was excised from pcCSF-17 and ligated into M13 for site-specific mutagenesis using the primer:

5'-G A G G G A T C C T G A T C A C C G C A G C T C C-3'.

This results in a new BclI site at codohs 159–160. The mutated DNA was excised with BstXI/EcoRI and ligated into the BstXI/EcoRI digested pcCSF-17, the ligation mixture was transformed in *E. coli* DG105, a dam-host, and the plasmid DNA isolated.

4. Verification of Construction

In the constructions set forth below, correct ligations for plasmid construction are confirmed by first transforming *E. coli* strain MM294, or other suitable host, with the ligation mixture. Successful transformants are selected by ampicillin, tetracycline or other antibiotic resistance or using other markers, depending on the mode of plasmid construction, as is understood in the art. Further screening of transformants is possible using the technique of colony hybridization essentially as described in Maniatis, T. et al. (supra pp. 312–328). Briefly, colonies were lifted onto nitrocellulose filters and sequentially placed on each of four Whatman filters each saturated with one of the following solutions: (1) in 10% SDS; (2) 0.5 MNaOH/1M NaCl; (3) 1.5M NaCl, 1.5M Tris pH 8.0; (4) 2×SSC for approximately 5 min. each. After cell lysis and binding the DNA, filters were prehybridized for 0.5–1 hr. at 42° C in hybridization buffer containing 30% formamide followed by hybridization for 1–2 hrs at 42° C. Filters were washed three times in 2×SSC and 0.1% SDS until background was reduced.

Plasmids from the transformants are then prepared according to the method of Clewell et al., 1969, *Proc. Natl. Acad. Sci, (USA)* 62:1159, optionally following chloramphenicol amplification (Clewell, 1972, *J. Bacteriol* 110:667). The isolated DNA is analyzed by restriction and/or sequenced by the dideoxy method of Sanger et al., 1977, *Proc. Natl. Acad. Sci. (USA)* 74:5463 as further described by Messing et al., 1981, *Nucleic Acids Res.* 9:309, or by the method of Maxam et al., 1980, *Methods in Enzymology* 65:499.

5. Transformation and Transfections

Depending on the host cell used, transformation is done using standard techniques appropriate to such cells. The calcium treatment employing calcium chloride, as described by Cohen, S. N. et al., 1972, *Proc. Natl. Acad. Sci. (USA)* 69:2110, and modifications as described by Hanahan, D., 1983, *J. Mol. Biol.*, 166:557–580 are used for procaryotes or other cells which contain substantial cell wall barriers. Infection with *Agrobacterium tumefaciens* (Shaw et al., 1983, *Gene* 23:315) is used for certain plant cells. Transformations into yeast are carried out according to the method of Van Solingen et al., 1977, *J. Bacteriol* 130:946 and Hsiao et al., 1979, *Proc. Natl. Acad. Sci. (USA)* 76:3829.

Several transfection techniques are available for mammalian cells without such cell walls. The calcium phosphate precipitation method of Graham and van der Eb, 1978, *Virology* 52:546 is one method. Transfection can be carded out using a modification (Wang et al., 1985, *Science* 228:149) of the calcium phosphate coprecipitation technique. Another transfection technique involves the use of DEAE-dextran (Sompayrac, L. M. et al., 1981, *Proc. Natl. Acad. Sci. USA* 78:7575–7578). Alternatively, Lipofection refers to a transfection method which uses a lipid matrix to transport plasmid DNA into the host cell. The lipid matrix referred to as Lipofectin™ Reagent is available from BRL. Lipofectin™ Reagent comprises an aqueous solution (deionized and sterile filtered water) containing 1 mg/ml of lipid (DOTMA:DOPE, 50:50). This liposome-mediated transfection was carried out essentially as described by Felgner, P. L. et al. (1987, *Proc. Natl. Acad. Sci. U.S.A.* 84:7413). Lipofectin™ Reagent and DNA were separately diluted into serum free media so as to avoid gross aggregation which can occur when either material is too concentrated. For example, with 0.5×10$^6$ cells seeded onto a 60 mm tissue culture dish. 1.5 ml of serum free media containing 1 to 20 μg of DNA and a second solution of 1.5 ml serum free media containing about 30 μg of Lipofectin™ were prepared. The diluted DNA and Lipofectin™ solutions were mixed and applied onto the cells. The transfection is inhibited by serum, so the cells were washed well with serum free media before adding the Lipofectin™/DNA mixture.

The cells were incubated at 37° C. for 3–24 hours, then 3 ml of media containing 10% serum was added. The incubation time, prior to serum addition required for optimum transfection will vary depending on the cell type and the media used. Transfection with HEPES buffered saline is more cytotoxic and, therefore, shorter incubation times must be used than with EMEM or DMEM; toxicity is somewhat higher when the cells are subconfluent. Particularly good results were obtained with a serum free media, Opti-MEM (GIBCO), using incubation times of up to 24 hours prior to serum addition. The cells were harvested and assayed as usual.

6. CSF Assays

A. Bone Marrow Proliferation

For the bone marrow stimulation assay, which measures biological activity of the colony stimulating-factor portion of the protein, bone marrow cells from BALB/c mice were treated with serial dilutions of the culture supernatants, and proliferation of the cells was measured by uptake of labeled thymidine, essentially as described by Moore et al., 1983, *J. Immunol*, 131:2374 and Prystowsky et al., 1984, *Am. J. Pathol.* 114:149. Briefly, nucleated bone marrow cells were incubated at $5\times10^4$ cells well in 96-well plates with dilutions of the samples being tested. After three days [$^3$H]-Thymidine (0.5 µCi/well was added and 6 hours later the cells were harvested and counted. The medium from induced MIA PaCa-2 cells was used as control. Specificity for M-CSF was confirmed by the ability of rabbit antisera raised against human urinary M-CSF to suppress thymidine uptake as disclosed in PCT Patent Publication No. WO 87/04607 published 14 Aug. 1986 incorporated herein by reference in its entirety and in Kawasaki, E. S. et al., supra.

B. Colony Stimulation

Colony stimulation assays were carried out essentially as described by Metcalf, D., (supra) and Stanley et al., 1972, *J. Lab. Clin. Med.* 79:657 using fetal calf serum (Ralph, P. et al., 1986, supra).

Bone marrow cell suspensions were prepared in bone marrow collecting fluid from the pooled femurs of two to three, two months old C57BL or BALB/c mice. Bone marrow collecting fluid consisted of double strength MEM-α medium, 40 ml; fetal calf serum, 10 ml; distilled $H_2O$, 50 ml.

To prepare the agar culture medium, equal volumes of culture medium and freshly boiled 0.6% Difco Bacto-agar in $H_2O$ were mixed at 37° C. and held at 37° C. The culture medium was prepared immediately before use by mixing the following: double strength MEM-α medium, 40 ml; fetal calf serum, 10 ml; DEAE dextran (Pharmacia, Sweden) (Dextran MW=$2\times10^6$/n/=0.70) 50 mgm/ml, 0.15 ml; L-asparagine 6.6 mgm/ml, 0.3 ml.

Sufficient bone marrow cells were added to the agar-medium to give final cell concentrations ranging from 25,000–75,000 cells per milliliter. Cultures were made in 35 mm plastic petri dishes (Falcon Labware, Oxnard, Calif.) and the source of colony stimulating factor (CSF) was pipetted into the empty petri dishes before the addition of 1 ml of the bone marrow cells in agar-medium. The cells in liquid agar-medium were mixed thoroughly with the source of CSF and the dishes allowed to gel at room temperature. Cultures were incubated for 1–7 days in a fully humidified atmosphere of 10% $CO_2$ in air.

Counting of cell aggregates were performed on unstained cultures with dissecting microscope at X 25 or 40 magnifications with indirect illumination. Colony size ranged from 50 to 2,000 cells depending on the concentration of CSF. Cytological examination of clusters and colony cells was performed by picking off cell aggregates with a fine Pasteur pipette and placing these on microscope slides. Colonies were stained with 0.6% orcein in 60% acetic acid and cells classified at X 400 or 1000 magnifications according to criteria described previously (Metcalf et al., 1967, *J. Natl. Canc. Instit.* 39:1235–1245). Alternatively, cell type was determined by cytocentrifuging individual colonies and staining with a modified Wright stain.

Direct assay of the COS-7 supernatants from cells transfected with pcCSF-17 for colony stimulation, for example, showed 4287 U/ml, which was substantially unaffected by the presence of non-immune serum but reduced to 0 U/ml in the presence of rabbit antihuman M-CSF. This compares to 2562 U/ml in the MIA PaCa-2 supernatants. Eighty-five percent of the pcCSF-17 transformed COS-7 supernatant induced colonies had mononuclear/macrophage morphology; MIA PaCa-2 supernatant induced colonies showed a 94% macrophage-6% granulocyte ratio.

C. Radioreceptor Assay (RRA) and Radioimmune Assay (RIA)

The radioreceptor assay measures competition between $^{125}$I-labeled M-CSF and the test compound for specific receptors on J774.2 mouse macrophage cells (Ralph, P. et al., 1986, supra; Das, S. K. et al., 1981, supra). MIA PaCa-2 supernatant, assayed for colony stimulating activity as above, was used as a standard (2000 U/ml). The M-CSF concentration of the pcCSF-17 transformed COS-7 supernatant was found to be 2470 U/ml based on a 1:10 dilution and 3239 U/ml based on a 1:5 dilution. Thus, comparable values for M-CSF concentration in the media of COS-7 cells transformed with pcCSF-17 were found in all assays.

An RIA which is specific for human M-CSF has also been described (Shadle, P. J. et al., 1989, *Exp. Hematol.* 17:154–159 incorporated herein by reference). Briefly, high liter antisera to human recombinant M-CSF protein allowed detection of as little as 60 U/ml (1.2 ng/ml) of human M-CSF. The assay consisted of incubating a mixture of 100 µl of standard, containing 1.2–37.0 ng/ml (60–1910 U/ml) of M-CSF, 100 µl control or sample, 20,000 cpm of [$^{125}$I]M-CSF, and 100 µl of diluted rabbit anti-M-CSF for 12–18 h at 4° C. The rabbit antiserum was diluted in 2.5% normal rabbit serum to bind 30%–60% of the added counts of labeled M-CSF under the assay conditions. An aliquot (50 µl) of goat anti-rabbit IgG, diluted to give optimal precipitation, was then added, and the mixture was incubated for 1 h at 21° C. In some assays, the method was modified by adding 0.5 ml of 7.38% polyethylene glycol in phosphate-buffered saline (PBS) with the goat antibody. A 1.5-ml volume of cold PBS, pH 7.2, was then added, and the bound tracer was separated from free counts by centrifugation at 2500 g for 20 min. The pellets were then counted for $^{125}$I using a gamma counter. Quantitation of the M-CSF in the samples was determined by comparison of the sample counts to the counts obtained from the standards.

D. M-NFS-60 Proliferation Assay

A 48 hour colorimetric assay for M-CSF biological activity has been developed using M-NFS-60 cell proliferation and MTT (3-(4,5-dimethylthiazol-2-yl)- 2, 5-diphenyl tetrazolium bromide; Sigma) staining in a 96-well tissue culture plate format. The NFS-60 murine retrovirus-induced myeloid leukemia cell line as isolated by Weinstein, Y. et al., (1986, *Proc. Natl. Acad. Sci. USA* 83:5010–5014) was adapted for growth dependence upon M-CSF. Cells were routinely grown in RPMI 1640 medium plus 10% FBS, 1% penicillin/streptomycin, 0.05 mM β-mercaptoethanol, 2 mM glutamine and 2,000 U/ml recombinant human M-CSF. Cells for use in the assay were in log phase growth. Cells were washed two times to remove exogenous M-CSF and diluted to $1\times10^5$ cells/ml in assay medium (growth medium without M-CSF). Wells in rows A to G of microliter plates were filled with 50 µl assay medium. Samples of unknown activity or standard M-CSF solution (50 µl) were loaded into column 1 of rows A–G. Serial dilutions (2-fold; 50 µl transfers) were made from columns 1–12 in rows A–G. Row H contained both blank wells lacking M-CSF and wells containing a maximally effective amount of M-CSF. Diluted cells were added (50 µl or $5\times10^3$ cells) to each well and plates were incubated 48 hrs at 37° C., 5% $CO_2$. Then, MTT stain (5 mg/ml) was added (25 µl) to each well. Plates were incubated at 37° C., 5% $CO_2$ for 3 hrs. Then 20% (w/v) SDS was added (100 µl/well) and plates wrapped tightly in plastic wrap and let stand at room temperature overnight in a light tight box. Well optical densities were read on a BIO-TEK EL310 plate reader at 570 nm.

M-NFS-60 cells proliferate in a dose dependent manner in response to M-CSF or murine IL-3 and also partially respond to G-CSF and murine GM-CSF. M-CSF activity of serially diluted samples are measured relative to a human recombinant M-CSF standard calibrated in a murine bone marrow colony formation assay. Assay results are reported in bone marrow colony forming units/mL (BMCFU/mL). The sensitivity of the M-NFS-60 proliferation assay is approximately 50 BMCFU/mL. The inter-assay precision was determined to be 17% RSD for 47 assays performed over a four month period.

7. IL-2 Assay—HT-2 Cell Proliferation

The proliferation of HT-2 mouse helper T-lymphocyte cells in response to IL-2 was measured by a [$^3$]thymidine ([$^3$]TdR) incorporation microassay, essentially as described by Gillis et al., 1978, *J. Immunol*, 120:2027–2032. The target cells were washed and resuspended at $2 \times 10^5$/ml in RPMI 1640 media containing 10% FBS. Equal volumes of cells and of serial dilutions of IL-2-containing samples were added to 96-well microtiter plates (Falcon/Becton-Dickinson Labware, Oxnard, Calif. U.S.A.). After 24 h incubation cultures were pulsed for 5 h with 1 µCi [$^3$H]TdR (specific activity, 70 Ci/mmol; New England Nuclear, Boston, Mass., U.S.A.), harvested onto Whatman GF/C filters (Whatman Laboratory Products, Inc., Clifton, N.J., U.S.A.), and radioactivity determined in a liquid scintillation counter. IL-2 activity of unknown samples are measured relative to a recombinant human IL-2 standard calibrated in International units.

8. Assays of Other Proteins

IL-1 is assayed by commercial Elisas (Cistron, Pine Brook, N.J.; Endogen, Boston, Mass.), by the production of IL-2 by LBRN-33 cells (Larrick, J. et al, 1985, *J. Immunol. Meth.* 79:39) or by the assays described in U.S. Pat. No. 4,808,611 and 4,801,686.

G-CSF, murine GM-CSF and IL-3 are assayed by the NFS-60 assay or the colony stimulation (BMCFU) assay described in Section 6. G-CSF is also measured by assays described in U.S. Pat. No. 4,810,643.

Murine IFN-γ is assayed for antiviral activity in a cytopathic effect inhibition assay (Stewart, W. E., II, 1979, *The Interferon System*, Springer:New York, pp. 13–145) with encephalomyocarditis virus as a challenge virus and murine L929 cells as the target. Human IFN-γ is assayed for antiviral activity as described in U.S. Pat. No. 4,762,791 in a standard cytopathic effect inhibition assay employing Vesicular Stomatitis Virus (VSV) or Encephalomyocarditis Virus on WISH (human amnion) cells as described by Stewart, supra.

IL-6 is assayed by a cell line specific assay (Helle, M. et al..1988, *Eur. J. Immunol.* 18:1535; Shimizu, S. et al., 1989, *J. Exp. Med.* 169:339).

9. Transient Expression of Fusion Proteins

The expression of plasmid DNAs containing M-CSF fusion genes in COS-$A_2$ cells was confirmed and quantitated using assays including the bone marrow proliferation assay, the colony stimulation assay, the radioreceptor assay and the M-NFS- 60 assay. It will be recalled that the specificity of the bone marrow proliferation assay for M-CSF resides only in the ability of M-CSF antiserum to diminish activity; that for the colony stimulation assay, in the nature of the colonies obtained. The fusion-encoding plasmids were transfected into COS-A2 cells and transient expression of M-CSF activity was assayed by the bone marrow proliferation or the M-NFS 60 proliferation assay and by radioimmunoassay using anti-CSF antibodies.

10. Suitable Hosts, Control Systems and Methods

In general terms, the production of a recombinant fusion form of M-CSF typically involves the following:

First, a DNA is obtained that encodes the fusion protein or preprotein. If the sequence is uninterrupted by introns it is suitable for expression in any host. If there are introns, expression is obtainable in mammalian or other eucaryotic systems capable of processing them. This sequence should be in excisable and recoverable form.

The excised or recovered coding sequence is then preferably placed in operable linkage with suitable control sequences in a replicable expression vector. The vector is used to transform a suitable host and the transformed host cultured under favorable conditions to effect the production of the recombinant M-CSF fusion protein. Optionally the M-CSF fusion protein is isolated from the medium or from the cells; recovery and purification of the protein may not be necessary in some instances, where some impurities may be tolerated. However, direct use in therapy by administration to a subject would, of come, require purification of the M-CSF fusion produced.

Each of the foregoing steps can be done in a variety of ways. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, insert, or mammalian cells are presently useful as host. Since native M-CSF is secreted as a glycosylated dimer, host systems which are capable of proper posts translation processing are preferred. Accordingly, although procaryotic hosts are in general the most efficient and convenient for the production of recombinant proteins, eucaryotic cells, and, in particular, mammalian cells or insect cells are preferred for their processing capacity. Recombinant M-CSF fusion proteins produced by bacteria may require in vitro dimerization. Such a process for the production of M-CSF proteins in their active form is disclosed in commonly owned PCT Publication No. WO 88/08003 published Oct. 20, 1988 incorporated herein by reference in its entirety. In addition, there is more assurance that the native signal sequence will be recognized by mammalian cell or insect cell hosts making secretion possible, and therefore purification easier.

Procaryotes most frequently are represented by various strains of *E. coli*. However, other microbial strains may also be used, such as bacilli, for example, *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., 1977, *Gene* 2:95. pBR322 contains genes for ampicillin and tetracycline resistance, and thus provides additional markers which can be either retained or destroyed in constructing the desired vector. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., 1977, *Nature* 198:1056), the tryptophan (trp) promoter system (Goeddel et al., 1980, *Nucleic Acids Res.* 8:4057) and the lambda derived $P_L$ promoter (Shimatake et al., 1981, *Nature* 292:128), and N-gene ribosome binding site, which has been made useful as a portable control cassette, U.S. Pat. No. 4,711,845, issued Dec. 8, 1987 and incorporated by reference in its entirety, which comprises a fast DNA sequence that is the $P_L$ promoter operably linked to a second DNA sequence corresponding to the $N_{RBS}$ upstream of a third DNA sequence having at least one restriction site that permits cleavage within 6 bp 3' of the $N_{RBS}$ sequence. U.S. Pat. No. 4,666,848 issued May 19, 1987 and incorporated herein by reference in its entirety discloses additional vectors with enhanced expression capabilities. Also useful is the phosphatase A (phoA) system described by Chang et al., in European Patent Publication No. 196,864, published Oct. 8, 1986, incorporated herein by reference. However, any available promoter system compatible with procaryotes can be used.

Multifunctional M-CSF fusion proteins are produced in *E. coli* preferably using the lambda $P_L$ promoter to direct expression. In a fusion protein having M-CSF at the amino-terminal end, the $N\nabla_3$ form is preferred for expression in *E. coli*. The C-terminus may, of course, also be truncated.

Recombinant M-CSF fusion proteins are recovered from *E. coli* as insoluble inclusion bodies or refractile material that are partially purified from the cell debris by centrifugation. SDS-PAGE analysis of the inclusion bodies, following alkylation or reduction, showed that most of the total M-CSF fusion protein has a monomeric molecular weight in the absence of reducing agents. This indicates that the majority of the M-CSF fusion protein in inclusion bodies is non-covalently aggregated.

The partially purified M-CSF fusion protein in the refractile material is solubilized in urea and purified by size exclusion HPLC (SEC-HPLC) under denaturing conditions. Following the purification of the reduced M-CSF fusion monomer, the M-CSF is refolded to its active form by diluting the urea concentration to less than 1M. In order to study M-CSF fusion protein refolding reactions at relatively high protein concentrations, the denatured, monomeric M-CSF fusion protein in the SEC-HPLC pool is concentrated 10-fold to a protein concentration of 5 mg/ml. M-CSF fusion protein refolding reactions are initiated by diluting the denatured M-CSF fusion monomer into cold refolding buffer at a final protein concentration of either 0.3 or 0.7 mg/ml. To promote disulfide bond formation and rearrangement, refolding reactions contain reduced and oxidized glutathione at a ratio of 2:1, respectively. When glutathione (and residual dithiothreitol) are excluded from the refolding reaction, the rate of M-CSF fusion protein dimerization slowed significantly, requiring five or more days of refolding to approach completion.

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, 1983, *Meth. Enz.* 101:307; U.S. Pat. No. 4,803,164 incorporated herein by reference in its entirety), other plasmid vectors suitable for yeast expression are known (see, for example, Stinchcomb et al., 1979, *Nature* 282:39, Tschempe et al., 1980, *Gene* 10:157 and Clarke et al., 1983, *Meth. Enz.* 101:300). Control sequences for yeast vectors include promoters for the synthesis of glycolytic enzymes (Hess et al., 1968, *J. Adv. Enzyme. Req.* 7:149; Holland et al., 1978, *Biochemistry* 17:4900).

Additional promoters useful in yeast host microorganisms and known in the art include the promoter for 3-phosphoglycerate kinase (Hitzeman et al., 1980, *J. Biol. Chem.* 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., 1981, *J. Biol. Chem.* 256:1385) or the LEU2 gene obtained form YEp13 (Broach et al., 1978, *Gene* 8:121); however, any vector containing a yeast compatible promoter, origin of replication and other control sequences is suitable.

It is also, of course, possible to express genes encoding proteins in eucaryotic host cell cultures derived from multicellular organisms. See, for example, *Tissue Culture* Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113) viral promoters such as those derived from polyoma, Adenovirus 2, bovine papilloma virus, or arian sarcoma viruses, or immunoglobulin promoters and heat shock promoters. A system for expressing DNA in mammalian systems using the BPV as a vector is disclosed in U.S. Pat. No. 4,419,446 incorporated herein by reference in its entirety. A modification of this system is described in U.S. Pat. No. 4,601,978 incorporated herein by reference in its entirety. General aspects of mammalian cell host system transformations have been described by Axel in U.S. Pat. No. 4,399,216 issued Aug. 16, 1983. Also useful is gene amplification in eucaryotic cells as described by Ringold in U.S. Pat. No. 4,656,134 issued Apr. 7, 1987 incorporated herein by reference in its entirety. It now appears also that "enhancer" regions are important in optimizing expression; these are, generally, sequences found upstream of the promoter region. Origins of replication may be obtained, if needed, from vital sources. However, integration into the chromosome is a common mechanism for DNA replication in eucaryotes.

Plant cells are also now available as hosts, and control sequence compatible with plant cells such as the nopaline synthase promoter and polyadenylation signal sequences (Depicker et al., 1982, *J. Mol. Appl. Gen.* 1:561) are available. Additionally, methods and vectors for transformation of plant cells have been disclosed in PCT Publication No. WO 85/04899 published Nov. 7, 1985 and incorporated herein by reference in its entirety.

11. Hosts Exemplified

Host strains used in cloning and expression herein are as follows:

For cloning and sequencing, and for expression of construction under control of most bacterial promoters, *E. coli* strain MM294 obtained from *E. coli* Genetic Stock Center GCSC #6135, was used as the host. For expression under control of the $P_LN_{RBS}$ promoter, *E. coli* strain K12 MC1000 lambda lysogen, $N_7N_{53}$cI857 SusP$_{80}$, a strain deposited with the American Type Culture Collection (ATCC 39531), may be used. *E. coli* DG116, which was deposited with the ATCC (ATCC 53606) on Apr. 7, 1987, may also be used.

For M13 phage recombinants, *E. coli* strains susceptible to phage infection, such as *E. coli* K12 strain DG98, are employed. The DG98 strain has been deposited with the ATCC (ATCC 39768) on Jul. 13, 1984.

Mammalian expression has been accomplished in COS-A2 cells and also can be accomplished in COS-7, and CV-1, hamster and murine cells. Insect cell-based expression can be in *Spodoptera frugiperda*.

EXAMPLES

The following examples are intended to illustrate but not to limit the invention.

Example I

A. Construction of pML1 Containing SCSF/C ∇158-IL-2 Fusion

The coding sequences encoded by of M-CSF and IL-2 were fused in such a way that the translational reading frame of each of the two proteins was preserved and the resulting fusion protein expressed from this hybrid gene had an amino terminal sequence derived from M-CSF and a carboxy-terminal sequence derived from IL-2. The fusion protein encoded in pML1 contains 158 amino acids of SCSF in addition to the secretory signal sequence at the amino-terminal end and 133 amino acids of IL-2 polypeptide at the carboxy-terminal end. Two additional amino acids were introduced at the fusion junction as a result of the gene construction used.

The plasmids used in the construction of pML1 included pcCSF-17 described in Kawasaki et al., 1985, Supra and deposited on June 14, 1985 having ATCC accession number 53,149. pRAIL102, a ricin A toxin/IL-2 fusion vector, was the source of the IL-2 coding sequence. It contained the following fusion sequence: 5' . . . GT TTT CTT TGC TTA TAA GGC CAA GTG CTT CCA GGC ACT GGA TCT GGC CCG CCG CCT CCG CCG CCT TCT GGA TCC GAG CTT *ATG CCT* . . . -3' wherein the italicized sequence is the spacer arm and the underlined sequence is the IL-2 coding sequence including a codon for an N-terminal methionine. The sequence 5' to the spacer arm derives from the ricin A and ricin junction peptide coding sequences (European Patent Publication No. 0145111 incorporated herein by reference in its entirety).

pRAIL 102 was constructed by subcloning the ricin A-spacer arm-IL-2 containing HindIII-BanII fragment from pRAIL101 into HindIII-BanII digested pPLOP (deposited Dec. 18, 1984 and having ATCC accession number 39947; also described in U.S. Pat. No. 4,677,063 incorporated herein by reference in its entirety). pRAIL101 was constructed by ligating KpnI digested pPLSA and HindIII digested (blunt ended with Klenow) pLW21 (similar to pLW1 and described in U.S. Pat. No. 4,518,584 and in Wang, A. et al., supra). Ampicillin resistant ($amp^R$) and chloramphenicol resistant ($cam^R$) transformants were selected and screened for orientation of the des-alanyl IL-2 gene downstream of the ricin A-spacer arm coding sequence. pPLSA contained the ricin A sequence which is encoded in pRA123 (disclosed in copending commonly owned U.S. Ser. No. 837,583, filed March 7, 1986 incorporated herein by reference in its entirety, and deposited August 17, 1984 and having ATCC accession number 39799) fused at the KpnI site (at codons for amino acids 7–9 of the dodecameric polypeptide linker and therefore preceding the termination codon) to a spacer arm having the sequence:

5'-CTTCCAGGCACTGGATCTGGCCCGCCGC-CTCCGCCGCC TTCTGGATCCGGTACCTGCT-GAGTCGAC-3'.

The BstXI-BamHI fragment of the BamBcl derivative of pcCSF-17 containing the M-CSF secretory leader and mature protein coding sequences through codon 158 as shown in FIG. 5 of Kawasaki et al., (supra) was isolated from a 1.2% agarose gel. The BamHI-BanII (Klenow repaired) fragment of pRAIL102 containing the des-ala IL-$2_{cys125}$ gene was also isolated from a 1.2% agarose gel. The vector fragment was from pcDB (Ladner, M. B. et al., 1988, *Proc. Natl. Acad. Sci. USA* 85:6706–6710), a derivative of the Okayama-Berg vector system (Okayama et al., 1982, *Mol. Cell. Biol.* 2:161 and in 1983, *Mol. Cell Biol.* 3:280–289) used in the construction of pcDBCSF-4 (deposited as ATCC accession No. 67250 on Oct. 24, 1986). The KpnI (Klenow repaired) BstXI fragment of pcDBCSF-4 (Ladner et al., 1987, supra) was prepared.

After ligation of the three fragments, *E. coli* MM294 was transformed and $Ap^R$ colonies were screened by colony hybridization. Labelled probe EK117 having the sequence 5'-GCTTTGAGCTAAATTTAGCACTTCCTGCAG-3' (codons 86–95 of the IL-2 gene) was used to identify candidate clones. The candidate designated pML1 was further confirmed to be the desired fusion by XbaI and BstXI double digestion of miniprep DNA.

The sequence across the fusion junction was predicted to be as follows:

```
<———————— M-CSF      IL-2 ————>
5'. . . AGG CAG TCC GAG GGA TCC GAG CTT ATG CCT . . . 3'
        Arg Gln Ser Glu Gly Ser Glu Leu Met Pro 3'
```

B. Expression of the Fusion Protein

Monkey COS-$A_2$ cells were transfected with pML1 and DNA containing M-CSF ($asp_{59}$SCSF/C$\nabla$158; PCT publication number WO86/04607) as a control. Cell culture medium was replaced after 16–24 hours and in an additional 48 hours, cell culture medium was harvested, cleared by centrifugation and frozen for further analysis. M-CSF protein in the culture supernatant was assayed by RIA and biological activity was measured in the colony proliferation assay. IL-2 activity was assayed by the HT-2 cell proliferation assay. The results are shown in the Table below.

| | M-CSF RIA U/ml | Bone Marrow Colony Assay U/ml | IL-2 Assay U/ml |
|---|---|---|---|
| M-CSF/IL-2 Transfection 1 | $2.4 \times 10^5$ | $5.7 \times 10^5$ | $4 \times 10^3$ |
| M-CSF/IL-2 Transfection 2 | $2.6 \times 10^5$ | $8.7 \times 10^5$ | $9.2 \times 10^3$ |
| pcCSF-17 $asp_{59}$CV 158 | $3.3 \times 10^5$ | $1.9 \times 10^6$ | 0 |
| MOCK | 40 | 0 | 0 |

FIG. 1 shows PAGE analysis of transfected COS cell supernatants after immunoaffinity isolation with rabbit anti-CSF antibody. Lanes 1–3 show unreduced immunoprecipitates from COS cell supernatants transfected with: lane 1, mock transfected cells, lane 2, pcCSF17/asp$_{59}$/ser$_{158}$/TGA, or lane 3, pML1. Lanes 7–9 show reduced immunoprecipitates from Cos cell supernatants transfected with: lane 7, mock transfected cells, lane 8, pcCSF17/asp$_{59}$/ser$_{158}$/TGA, or lane 9, pML1. Lanes 5 and 10 are molecular weight standards as indicated.

Example 2

A. Construction of pML2 Containing LCSF/C∇221—IL-2 Fusion

The fusion protein encoded by of pML2 contains 221 amino acids of LCSF in addition to its secretory signal sequence at the aminoterminal end and 133 amino acids of the mature IL-2 polypeptide at the carboxy-terminal end. The DNA encoding the fusion protein was derived using the polymerase chain reaction (PCR) which is described in Section B.2 herein above. The M-CSF coding sequence was amplified from pcDBCSF-4 (deposited Oct. 24, 1986 in the ATCC under accession number 67250) using primers GM54 and GM55 shown in Table I below. The IL-2 coding sequence was amplified from pML1 (deposited in the ATCC) using primers GM56 and GM57 also shown below.

TABLE I OF OLIGONUCLEOTIDE PRIMERS

GM54 5' GAATTCCATGACCGCGCCGGG 3'

GM55 5' AACTCGAGGTAGGTGCTGGCCGCTGCT-TGGC 3'

GM56 5' CCTCGAGTTCTACAAAGAAAACACAGC 3'

GM57 5' GCGGCCGCTTATCAAGTCAGTGTTGAG 3'

GM54 contains an EcoRI recognition site at its 5' end and hybridized to the 5' coding region of M-CSF on the coding strand of pcDBCSF-4. GM55 contains an XhoI recognition site at its 5' end and hybridized to the 3' end of the M-CSF coding sequence on the noncoding strand of pcDBCSF-4. PCR amplification resulted in an EcoRI-XhoI fragment containing the M-CSF coding sequence. Similarly, GM56 contains an XhoI recognition site at its 5' end and hybridized to the 5' end of the IL-2 gene on the coding strand of pML1. GM57 contains a NotI recognition site at its 5' end and hybridized to the 3' end of the IL-2 on the noncoding strand of pML1. PCR amplification and subsequent restriction enzyme digestion resulted in an XhoI-NotI fragment containing the IL-2 coding sequence.

Ligation of these two PCR-derived fragments into EcoRI and NotI double digested pcDB vector yielded pML2 after transformation into E. coli MM294. Transformants were screened by colony hybridization using GM55 and GM56 as probes and subsequent restriction analysis of miniprep DNAs confirmed the desired fusion construct. DNA sequence analysis of pML2 showed the following sequence spanning the junction of the M-CSF and IL-2 coding sequences.

```
               <—————————————— M-CSF  IL-2 ——>
5'... GTG GAT CCA GGC AGT GCC AAG CAG CGG CCA GCA CCT
      Val Asp Pro Gly Ser Ala Lys Gln Arg Pro Ala Pro
                                    ————————————————>
ACC TCG AGT TCT ACA AAG AAA ACA CAG...
Thr Ser Ser Ser Thr Lys Lys Thr Gln
```

B. Expression of the LCSF/C∇221-IL-2 Fusion Protein

Monkey COS-A2 cells were transfected using the lipofection and DEAE-dextran protocols with pML1 and pML2. Cell culture medium was replaced after 16–24 hours and in an additional 48 hours, cell culture medium was harvested, cleared by centrifugation and stored frozen. M-CSF protein in the culture supernatant was assayed by RIA and biological activity was measured in the M-NFS-60 assay. IL-2 activity was assayed by the HT-2 cell proliferation assay. The results are shown in the table below.

| | M-CSF RIA U/ml | M-CSF NFS 60 Bioassay U/ml | IL-2 Bioassay U/ml |
|---|---|---|---|
| A. Lipofection Transfection | | | |
| pML1 (158-IL-2) | $8 \times 10^3$ | $2.07 \times 10^4$ | $3.5 \times 10^3$ |
| pML2 (221-IL-2) | $1.5 \times 10^3$ | $3.9 \times 10^3$ | $8 \times 10^2$ |
| B. Deae - Dextran Transfection | | | |
| pML1 | $>3.6 \times 10^4$ | $1.2 \times 10^5$ | $2.1 \times 10^4$ |
| pML2 | $1 \times 10^4$ | $2.2 \times 10^4$ | $4.9 \times 10^3$ |
| MOCK | <559 | <310 | <2.24 |

Example 3

A. Construction of pML3 Containing LCSF/C∇221-IL-1α Fusion

The fusion protein of pML3 contains 221 amino acids of LCSF in addition to its secretory signal sequence at the amino-terminal end and amino acids 119 through 271 of human IL-1α. However any bioactive M-CSF or mutein thereof such as SCSF/C∇150, SCSF/C∇158 and amino-terminal deletions such as N∇3 of these or the LCSF molecules are expected to be appropriate for the construction of a dual signaling molecule. Similarly, any amino-terminal deletions of IL-1α may be used. It is known for example that amino acid residues through approximately 127 may be deleted and still retain IL-1α bioactivity (Mosley, B. et al. (1987) *Proc. Natl. Acad. Sci. USA* 84:4572–4576).

The DNA encoding the fusion protein is derived using PCR as described in Example 2. The M-CSF coding sequence is amplified from pML2 (deposited in the ATCC) using primers GM104 and GM101 shown in Table II below. The resulting 784 bp fragment has a unique BglII site at its 5' end and a unique AsuII site at its 3' end. In addition, the 3' end of this fragment overlaps with the IL-1 a coding region for 15 bp. The IL-1α coding region is amplified from pHl-1 (see A. Wang) using primer GM102 and GM103 also shown in Table II below. Amplification results in a 484 bp fragment having a 5' AsuII site and a 3' NotI site.

TABLE II OF OLIGONUCLEOTIDE PRIMERS

GM 101 5' TTTCACATTCGAAAGTGGCCGCTGCT-TGGCACTG 3'

GM 102 5' CAAGCAGCGGCCACTTTCGAATGT-GAAATACAAC 3'

GM 103 5' GGGCGGCCGCCTACGCCTGGTTTTC-
CAGTATC 3'

GM 104 5' CCAGATCTCCATGACCGCGCC 3'

After amplification, DNA fragments were cut with the appropriate restriction enzymes to generate cohesive termini. Following ligation of these fragments into BglII and NotI double digested pcDB vector, E. coli MM294 transformants were selected for Ap$^R$. Candidate clones were screened for fusion plasmids containing a single AsuII site, an approximately 1050 bp NotI/BstXI fragment and an approximately 36 bp AsuII/EcoRI fragment. The correct primary sequence across the M-CSF/IL-1α fusion boundary is confirmed by DNA sequence analysis. It is predicted to be:

⟵──────── M-CSF/IL-1α ────────⟶
5'...GGC AGT GCC AAG CAG CGG CCA CTT TCG AAT GTG AAA TAC AAC...3'
    Gly Ser Ala Lys Gln Arg Pro Leu Ser Asn Val Lys Tyr Asn

B. Expression of the LCSF/C-221-IL-1α

Monkey COS-A2 cells are transfected with pML3. Cell culture medium is replaced after 16–24 hours and in an additional 48 hours, cell culture medium is harvested, cleared by centrifugation and stored frozen. M-CSF protein in the culture supernatant is assayed by RIA and biological activity is measured in the M-NFS-60 assay. IL-1α is assayed by the assays described in U.S. Pat. Nos. 4,808,611 and 4,801,686.

Example 4

M-CSF/γ-IFN Fusion

A. Construction of pML4 Containing LCSF/C∇221-γ-IFN Fusion

The fusion protein encoded by pML4 contains 221 amino acids of LCSF in addition to its secretory signal sequence at the amino terminal end and amino acids 1 through 136 of murine γ-IFN. However any bioactive M-CSF or mutein thereof such as SCSF/C∇150, SCSF/C∇158 and amino-terminal deletions such as N∇3 of these or the LCSF molecules are expected to be appropriate for the construction of a dual signaling molecule. Similarly, amino-terminal deletions of γ-IFN may be used. Such a deletion for human γ-IFN is disclosed in U.S. Pat. No. 4,762,791.

The DNA encoding the fusion protein is derived using PCR as described in Example 2. The M-CSF coding sequence is amplified from pML2 using primers GM104 and MTL02 shown in Table HI below. The resulting 800 bp fragment has a unique BglII site at its 5' end and a unique KpnI site at its 3' end. In addition, the 3' end of this fragment overlaps with the IL-1α coding region for 15 bp. The γ-IFN coding region is amplified either from RNA from a γ-IFN producing cell or from a cDNA clone using primer MTL01 and MTL03 also shown in Table III below. Amplification results in a 442 bp fragment having a 5' KpnI site and a 3' NotI site.

TABLE III OF OLIGONUCLEOTIDE PRIMERS

GM 104 5' CCAGATCTCCATGACCGCGCC 3'

MTL01 5' GCAGCGGCCATGTTACTGCCACGGTAC-
CGTCATTGAAAGCC 3'

MTL02 5' GACGGTACCGTGGCAGTAACATGGC-
CGCTGCTTGGCACTGCC 3'

MTL03 5' GGGCGGCCGCCCGAATCAGCAGC-
GACTCC 3'

After amplification, DNA fragments were cut with the appropriate restriction enzymes to generate cohesive termini. Following ligation of these fragments to BglII and NotI double digested pcDB vector, E. coli MM294 transformants were selected for Ap$^R$. Candidate clones were screened for fusion plasmids containing a single KpnI site and an approximately 1184 bp BglII-NotI fragment. The correct primary sequence across the M-CSF/γ-IFN fusion boundary is confirmed by DNA sequence analysis. It is predicted to be:

⟵──────── M-CSF/IFN-γ ────────⟶
5'...GGC AGT GCC AAG CAG CGG CCA TGT TAC TGC CAC GGT ACC GTC...3'
    Gly Ser Ala Lys Gln Arg Pro Cys Tyr Cys His Gly Thr Val

B. Expression of the LCSF/C∇221-γ-IFN

Monkey COS-A$_2$ cells are transfected with pML4. Cell culture medium is replaced after 16–24 hours and in an additional 48 hours, cell culture medium is harvested, cleared by centrifugation and stored frozen. M-CSF protein in the culture supernatant is assayed by RIA and biological activity is measured in the NFS60 assay. γ-IFN is assayed by the assay described in Gray, P. W., et al. (supra).

Example 5

M-CSF/G-CSF Fusion

A. Construction of pML5 Containing LCSF/C∇221—G-CSF

The fusion protein encoded by pML5 contains 221 amino acids of LCSF in addition to its secretory signal sequence at the amino-terminal end and 174 amino acids of the mature G-CSF polypeptide at the carboxy-terminal end. The DNA encoding the fusion protein is derived using PCR as described in Example 2. The CSF coding sequence is amplified from pcDBCSF-4 (ATCC No. 67250) using primers GM 104 and GM 182 shown in Table V below. The resulting 790 bp fragment is digested with BglII which recognizes a site at the 5' end of the fragment and with XhoI having a site at the 3' end. The G-CSF coding sequence is amplified from pP12 (Devlin, J. J. et al., 1987, J. Leuk. Biol. 41:302–306) using primers GM 183 and GM 184 shown in Table IV. Other sources of the G-CSF sequence include the human bladder carcinoma cell line 5637 deposited under restrictive conditions as ATCC No. HTB-9 and pJD4A (ATCC No. 6718), pJD4B (ATCC No. 67185) and pPD5A (ATCC No. 67182). Amplification results in a 558 bp fragment having an XhoI site at the 5' end and a 3' KpnI site.

TABLE IV OF OLIGONUCLEOTIDE PRIMERS

GM 104 5' CCAGATCTCCATGACCGCGCC 3'

GM 182 5'GCTGGCAGGGCCCAGGGGGGTCGGC-
CGCTGCTTGGCACTGCC3'

GM 183 5'GGCAGTGCCAAGCAGCGGCCGAC-
CCCCCTGGGCCCTGCCAGC3'

GM 184 5'CCATGGTACCTGAT-
CAGGGCTGGGCAAGGTGGCGTAGAAC 3'

After amplification, DNA fragments were cut with the appropriate restriction enzymes to generate cohesive termini. Following ligation of these fragments into BglII and KpnI double digested pcDB vector, colonies are screened by colony hybridization to GM182 or GM183. The correct primary sequence across the M-CSF/G-CSF protein junction is confirmed by DNA sequence analysis. It is predicted to be:

$\longleftarrow$ M-CSF G-CSF $\longrightarrow$
5'... GGC AGT GCC AAG CAG CGG CCG ACC CCC CTG GGC CCT GCC AGC... 3'
    Gly Ser Ala Lys Gln Arg Pro Thr Pro Leu Gly Pro Ala B. Expression of the LCSF/C∇221-G-CSF Monkey COS-$A_2$ cells are transfected with pML5. Cell culture medium is replaced after 16–24 hours and in an additional 48 hours, cell culture medium is harvested, cleared by centrifugation and stored frozen. M-CSF protein in the culture supernatant is assayed by RIA and biological activity is measured in the M-NFS-60 assay. G-CSF is assayed by bone marrow proliferation and colony stimulation assays described in Section B.6 and in U.S. Pat. No. 4,810,643. Additional G-CSF assays including immunoassays and cell binding assays are disclosed in U.S. Pat. No. 4,810,643.

Example 6

M-CSF/IL-6 Fusion

A. Construction of pML6 Containing LCSF/C∇221-IL-6

The fusion protein encoded by pML6 contains 221 amino acids of LCSF in addition to its secretory signal sequence at the amino-terminal end and 183 amino acids of IL-6 at the carboxy-terminal end. The DNA encoding the fusion protein is amplified from pML2 as described in Example 2. The M-CSF coding sequence is amplified from pML2 using primers GM104 and GM190 as shown in Table V below. The resulting 814 bp PCR product is digested with BglII which recognizes a site at the 5' end of the fragment and XmaIII having a site at the 3' end. The IL-6 sequence is amplified either from RNA from an IL-6 producing cell line or from a cDNA clone using the primers GM187 and GM189 shown in Table V. Amplification results in a 587 bp fragment having a 5' XmaIII site and a 3' KpnI site.

TABLE V OF OLIGONUCLEOTIDE PRIMERS

GM 104 5' CCAGATCTCCATGACCGCGCC 3'

GM 187 5' CCAGGCAGTGCCAAGCAGCGGCCGGT-
TCCCCCAGGAGAAGATTCC 3'

GM 190 5' GGAATCTTCTGGGGGAACCGGCCGCF-
GCTGGCACTGCCTGG 3'

GM 189 5' ATGGTACCTTACTACATTTGCCGAA-
GAGCCCTCAG 3'

After amplification, DNA fragments were cut with the appropriate restriction enzymes to generate cohesive termini. Following ligation of these fragments into BglII and KpnI digested pcDB vector, colonies are screened by colony hybridization to GM187 or GM 190. The correct primary sequence across the M-CSF/IL-6 junction is confirmed by DNA sequence analysis. It is predicted to be:

$\longleftarrow$ M-CSF IL-6 $\longrightarrow$
5'... GGC AGT GCC AAG CAG CGG CCG GTT CCC CCA GGA GAA GAT TCC... 3'
    Gly Ser Ala Lys Gln Arg Pro Val Pro Pro Gly Glu Asp Ser B. Expression of the LCSF/C∇221-IL-6

Monkey COS-A2 cells are transfected with pML6. Cell culture medium is replaced after 16–24 hours and in an additional 48 hours, cell culture medium is harvested, cleared by centrifugation and stored frozen. M-CSF protein in the culture supernatant is assayed by RIA and biological activity is measured in the M-NFS-60 assay. IL-6 is assayed by the method of Helle, M., et al. (supra) or Shimizu, S. et al. (supra).

The following is a list of plasmids which may be useful in practicing the present invention.

| Plasmid | ATCC No. | Deposit Date | CMCC No. |
| --- | --- | --- | --- |
| pcDBCSF-4 | 67250 | October 24, 1986 | |
| pcCSF-17 | 53149 | June 14, 1985 | |
| pcCSF17asp$_{59}$ | 67139 | June 19, 1986 | |
| pcCSF-17gln$_{52}$ | 67140 | June 19, 1986 | |
| pcCSF-17pro$_{52}$ | 67141 | June 19, 1986 | |
| pcCSF-17-Bam | 67142 | June 19, 1986 | |
| pcCSF-17-BamBcl | 67144 | June 19, 1986 | |
| pcCSF-17gly$_{152}$ | 67145 | June 19, 1986 | |
| pLW1 (IL-2) | 39405 | | |
| pLW55 (IL-2) | 39516 | | |
| pLW45 (IL-2) | 39626 | | |
| pJD4A (G-CSF) | 67181 | August 12, 1986 | |
| pJD4B (G-CSF) | 67183 | August 12, 1986 | |
| pPD5A (G-CSF) | 67182 | August 12, 1986 | |
| IL-1α | 39997 | | |
| IL-1β | 39925 | | |
| pML1 | 67930 | April 18, 1989 | 3584 |
| pML2 | 67931 | April 18, 1989 | 3585 |
| pcDB | | | 3583 |

The address of the ATCC depository is as follows: The American Type Culture Collection, 12301 Parklawn Drive, Rockville, Md. 20852.

These deposits were made for the convenience of the relevant public and do not constitute an admission that a written description would not be sufficient to permit practice of the invention or an intention to limit the invention to these specific constructs. Set forth hereinabove is a complete written description enabling a practitioner of ordinary skill to duplicate the constructs deposited and to construct alternative forms of DNA, or organisms containing it, which permit practice of the invention as claimed.

The scope of the invention is no/to be construed as limited by the illustrative embodiments set forth herein, but is to be determined in accordance with the appended claims.

What is claimed is:

1. An isolated DNA encoding a multifunctional fusion protein having an M-CSF component and second bioactive component, wherein said DNA comprises a portion encoding an M-CSF protein capable of stimulating formation of primarily macrophage colonies in the in vitro colony-stimulating assay, which portion is in frame with a portion encoding a second bioactive protein selected from the group consisting of IL-1, IL-2, IFN-γ, and G-CSF, said M-CSF protein having amino acids 1 to 522 of SEQ ID NO: 2 or amino acids 1 to 224 of SEQ ID NO: 4 or being a biologically active fragment thereof, said fragment thereof having M-CSF activity and an N-terminus that begins with an amino acid residue at a position that is a member of the group consisting of positions 1, 2, 3 and 4 of SEQ ID NOS: 2 and 4, and having C-terminus that ends with an amino acid residue at a position that is a member of the group consisting of positions 150, 158, 190, 221 and 224 of SEQ ID NOS: 2 and 4, and 522 of SEQ ID NO: 2;

said second bioactive protein having the provisions: when the second bioactive protein is IL-1, said IL-1 protein comprises amino acid residues 127 through 271 of human IL-1α or amino acid residues 1 through 147 of human IL-1β as shown in SEQ ID NO: 8; when said second bioactive protein is IL-2, said IL-2 protein comprises amino acid residues 12 through 127 of SEQ ID NOS: 5 or 6, said fusion protein being capable of stimulating the proliferation of T-lymphocytes; when said second bioactive protein is IFN-γ, said IFN-γ protein comprises amino acid residues 6 through 127 of human IFN-γ as shown in SEQ ID NO: 9, said fusion protein having IFN-γ activity; and when said second bioactive protein is G-CSF, said G-CSF protein comprises amino acid residues 1 through 163 of recombinant G-CSF as shown in SEQ ID NO: 7, said fusion protein capable of stimulating the production of primarily neutrophil colonies of neutrophil-macrophage colonies in a colony forming assay using bone marrow progenitor cells of a species in which stimulation is to be effected.

2. The isolated DNA of claim 1 wherein said second bioactive protein is IL-2.

3. A cell culture transformed with a recombinant vector containing the DNA of claim 2 and capable of expressing the encoded fusion protein.

4. The isolated DNA of claim 1, wherein said M-CSF protein is encoded 5' to DNA encoding IL-2.

5. An isolated DNA comprising a coding sequence of the DNA of claim 1 or the complement thereto.

6. A cell culture transformed with a recombinant vector containing the DNA of claim 1 and capable of expressing the encoded fusion protein.

7. An isolated cell transformed with an expression vector containing the DNA of claim 1 and capable of expressing the encoded protein.

8. A vector encoding a multifunctional fusion protein, said vector being selected from the group consisting of pML1 and pML2.

9. An isolated DNA encoding a multifunctional fusion protein, said DNA comprising a portion encoding an M-CSF protein capable of stimulating formation of primarily macrophage colonies in an in vitro colony-stimulating assay, which portion is in frame with a portion encoding a second bioactive protein, said second bioactive protein being IL-2, said M-CSF protein having an amino acid sequence comprising Glu- Tyr-Cys-Ser-His-Met-Ile-Gly-Ser-Gly-His-Leu-Gln-Ser-Leu-Gln-Arg-Leu-Ile-Asp-Ser-Gln-Met-Glu-Thr-Ser-Cys-Gln-Ile-Thr-Phe-Glu-Phe-Val-Asp-Gln-Glu-Gln-Leu-Lys- Asp-Pro-Val-Cys-Tyr-Leu-Lys-Lys-Ala-Phe-Leu-Leu-Val-Gln-Asp-Ile-Met-Glu-Asp- Thr-Met-Arg-Phe-Arg-Asp-Asn-Thr-Pro-Asn-Ala-Ile-Ala-Ile-Val-Gln-Leu-Gln-Glu- Leu-Ser-Leu-Arg-Leu-Lys-Ser-Cys-Phe-Thr-Lys-Asp-Tyr-Glu-Glu-His-Asp-Lys-Ala- Cys-Val-Arg-Thr-Phe-Tyr-Glu-Thr-Pro-Leu-Gln-Leu-Leu-Glu-Lys-Val-Lys-Asn-Val- Phe-Asn-Glu-Thr-Lys-Asn-Leu-Leu-Asp-Lys-Asp-Trp-Asn-Ile-Phe-Ser-Lys-Asn-Cys- Asn-Asn-Ser-Phe-Ala-Glu, and said IL-2 having an amino acid sequence comprising Thr-Lys-Lys-Thr-Gln-Leu-Gln-Leu-Glu-His-Leu-Leu-Leu-Asp-Leu-Gln- Met-Ile-Leu-Asn-Gly-Ile-Asn-Asn-Tyr-Lys-Asn-Pro-Lys-Leu-Thr-Arg-Met-Leu-Thr- Phe-Lys-Phe-Tyr-Met-Pro-Lys-Lys-Ala-Thr-Glu-Leu-Lys-His-Leu-Gln-Cys-Leu-Glu- Glu-Glu-Leu-Lys-Pro-Leu-Glu-Glu-Val-Leu-Asn-Leu-Ala-Gln-Ser-Lys-Asn-Phe-His-Leu-Arg-Pro-Arg-Asp-Leu-Ile-Ser-Asn-Ile-Asn-Val-Ile-Val-Leu-Glu-Leu-Glu-Thr-Thr-Phe-Met-Cys-Glu-Tyr-Ala-Asp-Glu-Thr-Ala-Thr-Ile-Val-Glu-Phe-Leu- Asn-Arg-Trp-Ile-Thr-Phe-Cys-Gln-Ser-Ile-Ile-Ser-Thr-Leu-Thr.

10. An isolated DNA comprising a coding sequence of the DNA of claim 9.

11. A vector which comprises the DNA of claim 9 operably linked to suitable control sequences.

12. A DNA encoding a multifunctional fusion protein having an M-CSF component and an IL-2 component, said DNA comprising a first portion encoding an M-CSF protein capable of stimulating formation of primarily macrophage colonies in an in vitro colony-stimulating assay, which portion is in frame with a second portion encoding an IL-2 protein capable of stimulating the proliferation of helper T-lymphocytes, said M-CSF protein having amino acids 1 to 522 of SEQ ID NO: 2, amino acids 1 to 224 of SEQ ID NO: 4 or being an M-CSF active fragment thereof, said M-CSF protein optionally having a serine residue at position 157, said fragment thereof having an N-terminus that begins with an amino acid residue at a position that is a member of the group consisting of positions 1, 2, 3 and 4 of SEQ ID NOS. 2 and 4, and having a C-terminus ending with an amino acid residue position that is a member of the group consisting of positions 150, 158, 190, 221, and 224 of SEQ ID NOS: 2 and 4 and 522 of SEQ ID NO: 2; said IL-2 protein having the amino acid sequence of SEQ ID NO: 5 or SEQ ID NO: 6 with the provisos that one or more of the amino acid residues at positions 1 through 15 or 128 through 133 may be independently deleted or replaced, and that the amino acid residue at position 125 may be serine.

13. The DNA of claim 12 encoding for a multi-functional fusion protein wherein the portion encoding for said M-CSF protein is at the 5' end of said DNA and the portion encoding for said 1L-2 protein is at the 3' end of said DNA.

14. The DNA of claim 13 encoding for a multi-functional fusion protein wherein said M-CSF component is a M-CSF fragment having an N-terminus that lacks the amino acid residues at positions 1, 2, and 3.

15. The DNA of claim 14 encoding for a multi-functional fusion protein wherein said M-CSF fragment has a C-terminus ending with the amino acid residue at position 221.

16. The DNA of claim 15 encoding for a multi-functional fusion protein wherein said M-CSF fragment has a sequence in accordance with the amino acid residues at positions 4 through 221 of SEQ ID NO: 2.

17. The DNA of claim 14 encoding for a multi-functional fusion protein wherein said M-CSF fragment has a C-terminus ending with the amino acid residue at position 150.

18. The DNA of claim 17 encoding for a multi-functional fusion protein wherein said M-CSF fragment has a sequence in accordance with the amino acid residues at positions 4 through 150 of SEQ ID NO: 2.

19. The DNA of claim 14 encoding for a multi-functional fusion protein wherein said M-CSF fragment has a C-terminus ending with the amino acid residue at position 158.

20. The DNA of claim 19 encoding for a multi-functional fusion protein wherein said M-CSF fragment has a sequence in accordance with the amino acid residues at positions 4 through 158 of SEQ ID NO: 2.

21. The DNA of claim 12 encoding for a multi-functional fusion protein wherein said IL-2 component is an IL-2 protein of SEQ ID NO: 5 with the proviso that one or more amino acid residues at positions 1 through 15 or 128 through 133 from the N-terminus may be independently deleted or replaced.

22. The DNA of claim 12 encoding for a multi-functional fusion protein wherein said IL-2 component is an IL-2 protein of SEQ ID NO: 5 wherein amino acid residue at position 125 is serine or the N-terminal alanine is deleted, or both.

23. The DNA of claim 12 encoding for a multi-functional fusion protein wherein said IL-2 component is an IL-2 protein of SEQ ID NO: 6 with the proviso that one or more amino acid residues at positions 1 through 15 or 128 through 133 from the N-terminus may be independently deleted or replaced.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 2302 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 3..1610

( i x ) FEATURE:
( A ) NAME/KEY: mat_peptide
( B ) LOCATION: 45..1610

( x i ) SEQUENCE DESCRIPTION: SEQ ID NO:1:

```
CC  CTG  CTG  TTG  TTG  GTC  TGT  CTC  CTG  GCG  AGC  AGG  AGT  ATC  ACC  GAG                47
    Leu  Leu  Leu  Leu  Val  Cys  Leu  Leu  Ala  Ser  Arg  Ser  Ile  Thr  Glu
    -14            -10                      -5                            1

GAG  GTG  TCG  GAG  TAC  TGT  AGC  CAC  ATG  ATT  GGG  AGT  GGA  CAC  CTG  CAG                95
Glu  Val  Ser  Glu  Tyr  Cys  Ser  His  Met  Ile  Gly  Ser  Gly  His  Leu  Gln
                5                        10                       15

TCT  CTG  CAG  CGG  CTG  ATT  GAC  AGT  CAG  ATG  GAG  ACC  TCG  TGC  CAA  ATT               143
Ser  Leu  Gln  Arg  Leu  Ile  Asp  Ser  Gln  Met  Glu  Thr  Ser  Cys  Gln  Ile
              20                       25                       30

ACA  TTT  GAG  TTT  GTA  GAC  CAG  GAA  CAG  TTG  AAA  GAT  CCA  GTG  TGC  TAC               191
Thr  Phe  Glu  Phe  Val  Asp  Gln  Glu  Gln  Leu  Lys  Asp  Pro  Val  Cys  Tyr
         35                      40                       45

CTT  AAG  AAG  GCA  TTT  CTC  CTG  GTA  CAA  GAC  ATA  ATG  GAG  GAC  ACC  ATG               239
Leu  Lys  Lys  Ala  Phe  Leu  Leu  Val  Gln  Asp  Ile  Met  Glu  Asp  Thr  Met
 50                       55                       60                       65

CGC  TTC  AGA  GAT  AAC  ACC  CCC  AAT  GCC  ATC  GCC  ATT  GTG  CAG  CTG  CAG               287
Arg  Phe  Arg  Asp  Asn  Thr  Pro  Asn  Ala  Ile  Ala  Ile  Val  Gln  Leu  Gln
                   70                       75                       80

GAA  CTC  TCT  TTG  AGG  CTG  AAG  AGC  TGC  TTC  ACC  AAG  GAT  TAT  GAA  GAG               335
Glu  Leu  Ser  Leu  Arg  Leu  Lys  Ser  Cys  Phe  Thr  Lys  Asp  Tyr  Glu  Glu
              85                       90                       95

CAT  GAC  AAG  GCC  TGC  GTC  CGA  ACT  TTC  TAT  GAG  ACA  CCT  CTC  CAG  TTG               383
His  Asp  Lys  Ala  Cys  Val  Arg  Thr  Phe  Tyr  Glu  Thr  Pro  Leu  Gln  Leu
              100                      105                      110

CTG  GAG  AAG  GTC  AAG  AAT  GTC  TTT  AAT  GAA  ACA  AAG  AAT  CTC  CTT  GAC               431
Leu  Glu  Lys  Val  Lys  Asn  Val  Phe  Asn  Glu  Thr  Lys  Asn  Leu  Leu  Asp
     115                      120                      125

AAG  GAC  TGG  AAT  ATT  TTC  AGC  AAG  AAC  TGC  AAC  AAC  AGC  TTT  GCT  GAA               479
Lys  Asp  Trp  Asn  Ile  Phe  Ser  Lys  Asn  Cys  Asn  Asn  Ser  Phe  Ala  Glu
130                       135                      140                      145

TGC  TCC  AGC  CAA  GAT  GTG  GTG  ACC  AAG  CCT  GAT  TGC  AAC  TGC  CTG  TAC               527
Cys  Ser  Ser  Gln  Asp  Val  Val  Thr  Lys  Pro  Asp  Cys  Asn  Cys  Leu  Tyr
                   150                      155                      160

CCC  AAA  GCC  ATC  CCT  AGC  AGT  GAC  CCG  GCC  TCT  GTC  TCC  CCT  CAT  CAG               575
Pro  Lys  Ala  Ile  Pro  Ser  Ser  Asp  Pro  Ala  Ser  Val  Ser  Pro  His  Gln
                   165                      170                      175
```

```
CCC CTC GCC CCC TCC ATG GCC CCT GTG GCT GGC TTG ACC TGG GAG GAC     623
Pro Leu Ala Pro Ser Met Ala Pro Val Ala Gly Leu Thr Trp Glu Asp
        180             185                     190

TCT GAG GGA ACT GAG GGC AGC TCC CTC TTG CCT GGT GAG CAG CCC CTG     671
Ser Glu Gly Thr Glu Gly Ser Ser Leu Leu Pro Gly Glu Gln Pro Leu
    195                 200                     205

CAC ACA GTG GAT CCA GGC AGT GCC AAG CAG CGG CCA CCC AGG AGC ACC     719
His Thr Val Asp Pro Gly Ser Ala Lys Gln Arg Pro Pro Arg Ser Thr
210                     215                 220                 225

TGC CAG AGC TTT GAG CCG CCA GAG ACC CCA GTT GTC AAG GAC AGC ACC     767
Cys Gln Ser Phe Glu Pro Pro Glu Thr Pro Val Val Lys Asp Ser Thr
                230                     235                 240

ATC GGT GGC TCA CCA CAG CCT CGC CCC TCT GTC GGG GCC TTC AAC CCC     815
Ile Gly Gly Ser Pro Gln Pro Arg Pro Ser Val Gly Ala Phe Asn Pro
                    245                 250                 255

GGG ATG GAG GAT ATT CTT GAC TCT GCA ATG GGC ACT AAT TGG GTC CCA     863
Gly Met Glu Asp Ile Leu Asp Ser Ala Met Gly Thr Asn Trp Val Pro
            260                 265                 270

GAA GAA GCC TCT GGA GAG GCC AGT GAG ATT CCC GTA CCC CAA GGG ACA     911
Glu Glu Ala Ser Gly Glu Ala Ser Glu Ile Pro Val Pro Gln Gly Thr
    275                 280                     285

GAG CTT TCC CCC TCC AGG CCA GGA GGG GGC AGC ATG CAG ACA GAG CCC     959
Glu Leu Ser Pro Ser Arg Pro Gly Gly Gly Ser Met Gln Thr Glu Pro
290                     295                 300                 305

GCC AGA CCC AGC AAC TTC CTC TCA GCA TCT TCT CCA CTC CCT GCA TCA    1007
Ala Arg Pro Ser Asn Phe Leu Ser Ala Ser Ser Pro Leu Pro Ala Ser
                310                     315                 320

GCA AAG GGC CAA CAG CCG GCA GAT GTA ACT GGT ACA GCC TTG CCC AGG    1055
Ala Lys Gly Gln Gln Pro Ala Asp Val Thr Gly Thr Ala Leu Pro Arg
                    325                 330                 335

GTG GGC CCC GTG AGG CCC ACT GGC CAG GAC TGG AAT CAC ACC CCC CAG    1103
Val Gly Pro Val Arg Pro Thr Gly Gln Asp Trp Asn His Thr Pro Gln
            340                 345                 350

AAG ACA GAC CAT CCA TCT GCC CTG CTC AGA GAC CCC CCG GAG CCA GGC    1151
Lys Thr Asp His Pro Ser Ala Leu Leu Arg Asp Pro Pro Glu Pro Gly
    355                 360                     365

TCT CCC AGG ATC TCA TCA CTG CGC CCC CAG GGC CTC AGC AAC CCC TCC    1199
Ser Pro Arg Ile Ser Ser Leu Arg Pro Gln Gly Leu Ser Asn Pro Ser
370                     375                 380                 385

ACC CTC TCT GCT CAG CCA CAG CTT TCC AGA AGC CAC TCC TCG GGC AGC    1247
Thr Leu Ser Ala Gln Pro Gln Leu Ser Arg Ser His Ser Ser Gly Ser
                390                     395                 400

GTG CTG CCC CTT GGG GAG CTG GAG GGC AGG AGG AGC ACC AGG GAT CGG    1295
Val Leu Pro Leu Gly Glu Leu Glu Gly Arg Arg Ser Thr Arg Asp Arg
            405                 410                     415

AGG AGC CCC GCA GAG CCA GAA GGA GGA CCA GCA AGT GAA GGG GCA GCC    1343
Arg Ser Pro Ala Glu Pro Glu Gly Gly Pro Ala Ser Glu Gly Ala Ala
            420                 425                 430

AGG CCC CTG CCC CGT TTT AAC TCC GTT CCT TTG ACT GAC ACA GGC CAT    1391
Arg Pro Leu Pro Arg Phe Asn Ser Val Pro Leu Thr Asp Thr Gly His
435                     440                     445

GAG AGG CAG TCC GAG GGA TCC TCC AGC CCG CAG CTC CAG GAG TCT GTC    1439
Glu Arg Gln Ser Glu Gly Ser Ser Ser Pro Gln Leu Gln Glu Ser Val
450                     455                 460                 465

TTC CAC CTG CTG GTG CCC AGT GTC ATC CTG GTC TTG CTG GCC GTC GGA    1487
Phe His Leu Leu Val Pro Ser Val Ile Leu Val Leu Leu Ala Val Gly
                470                 475                 480

GGC CTC TTG TTC TAC AGG TGG AGG CGG CGG AGC CAT CAA GAG CCT CAG    1535
Gly Leu Leu Phe Tyr Arg Trp Arg Arg Arg Ser His Gln Glu Pro Gln
            485                 490                 495
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| AGA | GCG | GAT | TCT | CCC | TTG | GAG | CAA | CCA | GAG | GGC | AGC | CCC | CTG | ACT | CAG | 1583 |
| Arg | Ala | Asp | Ser | Pro | Leu | Glu | Gln | Pro | Glu | Gly | Ser | Pro | Leu | Thr | Gln |      |
|     |     | 500 |     |     |     | 505 |     |     |     |     |     | 510 |     |     |     |      |

|     |     |     |     |     |     |     |            |            |      |
|-----|-----|-----|-----|-----|-----|-----|------------|------------|------|
| GAT | GAC | AGA | CAG | GTG | GAA | CTG | CCA | GTG | TAGAGGGAAT | TCTAAGACCC | 1630 |
| Asp | Asp | Arg | Gln | Val | Glu | Leu | Pro | Val |            |            |      |
|     |     | 515 |     |     |     | 520 |     |     |            |            |      |

| | | | | |
|---|---|---|---|---|
| CTCACCATCC | TGGACACACT | CGTTTGTCAA | TGTCCCTCTG | AAAATGTGAC | GCCCAGCCCC | 1690 |
| GGACACAGTA | CTCCAGATGT | TGTCTGACCA | GCTCAGAGAG | AGTACAGTGG | GACTGTTACC | 1750 |
| TTCCTTGATA | TGGACAGTAT | TCTTCTATTT | GTGCAGATTA | AGATTGCATT | AGTTTTTTTC | 1810 |
| TTAACAACTG | CATCATACTG | TTGTCATATG | TTGAGCCTGT | GGTCTATTAA | AACCCCTAGT | 1870 |
| TCCATTTCCC | ATAAACTTCT | GTCAAGCCAG | ACCATCTCTA | CCCTGTACTT | GGACAACTTA | 1930 |
| ACTTTTTTAA | CCAAAGTGCA | GTTTATGTTC | ACCTTTGTTA | AAGCCACCTT | GTGGTTTCTG | 1990 |
| CCCATCACCT | GAACCTACTG | AAGTTGTGTG | AAATCCTAAT | TCTGTCATCT | CCGTAGCCCT | 2050 |
| CCCAGTTGTG | CCTCCTGCAC | ATTGATGAGT | GCCTGCTGTT | GTCTTTGCCC | ATGTTGTTGA | 2110 |
| TGTAGCTGTG | ACCCTATTGT | TCCTCACCCC | TGCCCCCGC | CAACCCCAGC | TGGCCCACCT | 2170 |
| CTTCCCCCTC | CCACCCAAGC | CCACAGCCAG | CCCATCAGGA | AGCCTTCCTG | GCTTCTCCAC | 2230 |
| AACCTTCTGA | CTGCTCTTTT | CAGTCATGCC | CCTCCTGCTC | TTTTGTATTT | GGCTAATAGT | 2290 |
| ATATCAATTT | GC | | | | | 2302 |

(2) INFORMATION FOR SEQ ID NO:2:

(i) SEQUENCE CHARACTERISTICS:
  (A) LENGTH: 536 amino acids
  (B) TYPE: amino acid
  (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Leu | Leu | Leu | Leu | Val | Cys | Leu | Leu | Ala | Ser | Arg | Ser | Ile | Thr | Glu | Glu |
| -14 | | | | -10 | | | | | -5 | | | | | | 1 |
| Val | Ser | Glu | Tyr | Cys | Ser | His | Met | Ile | Gly | Ser | Gly | His | Leu | Gln | Ser |
| | | 5 | | | | | 10 | | | | | 15 | | | |
| Leu | Gln | Arg | Leu | Ile | Asp | Ser | Gln | Met | Glu | Thr | Ser | Cys | Gln | Ile | Thr |
| | 20 | | | | | 25 | | | | | 30 | | | | |
| Phe | Glu | Phe | Val | Asp | Gln | Glu | Gln | Leu | Lys | Asp | Pro | Val | Cys | Tyr | Leu |
| 35 | | | | | 40 | | | | 45 | | | | | | 50 |
| Lys | Lys | Ala | Phe | Leu | Leu | Val | Gln | Asp | Ile | Met | Glu | Asp | Thr | Met | Arg |
| | | | | 55 | | | | | 60 | | | | | 65 | |
| Phe | Arg | Asp | Asn | Thr | Pro | Asn | Ala | Ile | Ala | Ile | Val | Gln | Leu | Gln | Glu |
| | | | 70 | | | | | 75 | | | | | 80 | | |
| Leu | Ser | Leu | Arg | Leu | Lys | Ser | Cys | Phe | Thr | Lys | Asp | Tyr | Glu | Glu | His |
| | | 85 | | | | | 90 | | | | | 95 | | | |
| Asp | Lys | Ala | Cys | Val | Arg | Thr | Phe | Tyr | Glu | Thr | Pro | Leu | Gln | Leu | Leu |
| | 100 | | | | | 105 | | | | | 110 | | | | |
| Glu | Lys | Val | Lys | Asn | Val | Phe | Asn | Glu | Thr | Lys | Asn | Leu | Leu | Asp | Lys |
| 115 | | | | | 120 | | | | 125 | | | | | | 130 |
| Asp | Trp | Asn | Ile | Phe | Ser | Lys | Asn | Cys | Asn | Asn | Ser | Phe | Ala | Glu | Cys |
| | | | | 135 | | | | | 140 | | | | | 145 | |
| Ser | Ser | Gln | Asp | Val | Val | Thr | Lys | Pro | Asp | Cys | Asn | Cys | Leu | Tyr | Pro |
| | | | 150 | | | | | 155 | | | | | 160 | | |
| Lys | Ala | Ile | Pro | Ser | Ser | Asp | Pro | Ala | Ser | Val | Ser | Pro | His | Gln | Pro |
| | | | 165 | | | | | 170 | | | | | 175 | | |

```
Leu Ala Pro Ser Met Ala Pro Val Ala Gly Leu Thr Trp Glu Asp Ser
    180             185             190
Glu Gly Thr Glu Gly Ser Ser Leu Leu Pro Gly Glu Gln Pro Leu His
195             200             205             210
Thr Val Asp Pro Gly Ser Ala Lys Gln Arg Pro Pro Arg Ser Thr Cys
            215             220             225
Gln Ser Phe Glu Pro Pro Glu Thr Pro Val Val Lys Asp Ser Thr Ile
        230             235             240
Gly Gly Ser Pro Gln Pro Arg Pro Ser Val Gly Ala Phe Asn Pro Gly
        245             250             255
Met Glu Asp Ile Leu Asp Ser Ala Met Gly Thr Asn Trp Val Pro Glu
    260             265             270
Glu Ala Ser Gly Glu Ala Ser Glu Ile Pro Val Pro Gln Gly Thr Glu
275             280             285             290
Leu Ser Pro Ser Arg Pro Gly Gly Gly Ser Met Gln Thr Glu Pro Ala
            295             300             305
Arg Pro Ser Asn Phe Leu Ser Ala Ser Pro Leu Pro Ala Ser Ala
            310             315             320
Lys Gly Gln Gln Pro Ala Asp Val Thr Gly Thr Ala Leu Pro Arg Val
        325             330             335
Gly Pro Val Arg Pro Thr Gly Gln Asp Trp Asn His Thr Pro Gln Lys
    340             345             350
Thr Asp His Pro Ser Ala Leu Leu Arg Asp Pro Pro Glu Pro Gly Ser
355             360             365             370
Pro Arg Ile Ser Ser Leu Arg Pro Gln Gly Leu Ser Asn Pro Ser Thr
            375             380             385
Leu Ser Ala Gln Pro Gln Leu Ser Arg Ser His Ser Ser Gly Ser Val
        390             395             400
Leu Pro Leu Gly Glu Leu Glu Gly Arg Arg Ser Thr Arg Asp Arg Arg
        405             410             415
Ser Pro Ala Glu Pro Glu Gly Gly Pro Ala Ser Glu Gly Ala Ala Arg
    420             425             430
Pro Leu Pro Arg Phe Asn Ser Val Pro Leu Thr Asp Thr Gly His Glu
435             440             445             450
Arg Gln Ser Glu Gly Ser Ser Ser Pro Gln Leu Gln Glu Ser Val Phe
            455             460             465
His Leu Leu Val Pro Ser Val Ile Leu Val Leu Leu Ala Val Gly Gly
        470             475             480
Leu Leu Phe Tyr Arg Trp Arg Arg Arg Ser His Gln Glu Pro Gln Arg
        485             490             495
Ala Asp Ser Pro Leu Glu Gln Pro Glu Gly Ser Pro Leu Thr Gln Asp
    500             505             510
Asp Arg Gln Val Glu Leu Pro Val
515             520
```

(2) INFORMATION FOR SEQ ID NO:3:

( i ) SEQUENCE CHARACTERISTICS:
        ( A ) LENGTH: 1642 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 179..946

( i x ) FEATURE:
    ( A ) NAME/KEY: mat_peptide
    ( B ) LOCATION: 275..946

( i x ) FEATURE:
    ( A ) NAME/KEY: -
    ( B ) LOCATION: 340
    ( D ) OTHER INFORMATION: /note="Intron Sequence"

( x i ) SEQUENCE DESCRIPTION: SEQ ID NO:3:

```
AGTGAGGCTC  GGCCCGGGGA  AAGTGAAAGT  TTGCCTGGGT  CCTCTCGGCG  CCAGAGCCGC        60

TCTCCGCATC  CCAGGACAGC  GGTGCGGCCC  TCGGCCGGGG  CGCCCACTCC  GCAGCAGCCA       120

GCGAGCGAGC  GAGCGAGCGA  GGGCGGCCGA  CGCGCCCGGC  CGGGACCCAG  CTGCCCGT         178
```

```
ATG  ACC  GCG  CCG  GGC  GCC  GCC  GGG  CGC  TGC  CCT  CCC  ACG  ACA  TGG  CTG    226
Met  Thr  Ala  Pro  Gly  Ala  Ala  Gly  Arg  Cys  Pro  Pro  Thr  Thr  Trp  Leu
-32       -30                      -25                     -20

GGC  TCC  CTG  CTG  TTG  TTG  GTC  TGT  CTC  CTG  GCG  AGC  AGG  AGT  ATC  ACC    274
Gly  Ser  Leu  Leu  Leu  Leu  Val  Cys  Leu  Leu  Ala  Ser  Arg  Ser  Ile  Thr
     -15                      -10                      -5

GAG  GAG  GTG  TCG  GAG  TAC  TGT  AGC  CAC  ATG  ATT  GGG  AGT  GGA  CAC  CTG    322
Glu  Glu  Val  Ser  Glu  Tyr  Cys  Ser  His  Met  Ile  Gly  Ser  Gly  His  Leu
 1                    5                    10                   15

CAG  TCT  CTG  CAG  CGG  CTG  ATT  GAC  AGT  CAG  ATG  GAG  ACC  TCG  TGC  CAA    370
Gln  Ser  Leu  Gln  Arg  Leu  Ile  Asp  Ser  Gln  Met  Glu  Thr  Ser  Cys  Gln
               20                       25                       30

ATT  ACA  TTT  GAG  TTT  GTA  GAC  CAG  GAA  CAG  TTG  AAA  GAT  CCA  GTG  TGC    418
Ile  Thr  Phe  Glu  Phe  Val  Asp  Gln  Glu  Gln  Leu  Lys  Asp  Pro  Val  Cys
          35                       40                       45

TAC  CTT  AAG  AAG  GCA  TTT  CTC  CTG  GTA  CAA  TAC  ATA  ATG  GAG  GAC  ACC    466
Tyr  Leu  Lys  Lys  Ala  Phe  Leu  Leu  Val  Gln  Tyr  Ile  Met  Glu  Asp  Thr
     50                       55                       60

ATG  CGC  TTC  AGA  GAT  AAC  ACC  CCC  AAT  GCC  ATC  GCC  ATT  GTG  CAG  CTG    514
Met  Arg  Phe  Arg  Asp  Asn  Thr  Pro  Asn  Ala  Ile  Ala  Ile  Val  Gln  Leu
65                       70                       75                       80

CAG  GAA  CTC  TCT  TTG  AGG  CTG  AAG  AGC  TGC  TTC  ACC  AAG  GAT  TAT  GAA    562
Gln  Glu  Leu  Ser  Leu  Arg  Leu  Lys  Ser  Cys  Phe  Thr  Lys  Asp  Tyr  Glu
                    85                       90                       95

GAG  CAT  GAC  AAG  GCC  TGC  GTC  CGA  ACT  TTC  TAT  GAG  ACA  CCT  CTC  CAG    610
Glu  His  Asp  Lys  Ala  Cys  Val  Arg  Thr  Phe  Tyr  Glu  Thr  Pro  Leu  Gln
               100                      105                      110

TTG  CTG  GAG  AAG  GTC  AAG  AAT  GTC  TTT  AAT  GAA  ACA  AAG  AAT  CTC  CTT    658
Leu  Leu  Glu  Lys  Val  Lys  Asn  Val  Phe  Asn  Glu  Thr  Lys  Asn  Leu  Leu
          115                      120                      125

GAC  AAG  GAC  TGG  AAT  ATT  TTC  AGC  AAG  AAC  TGC  AAC  AAC  AGC  TTT  GCT    706
Asp  Lys  Asp  Trp  Asn  Ile  Phe  Ser  Lys  Asn  Cys  Asn  Asn  Ser  Phe  Ala
     130                      135                      140

GAA  TGC  TCC  AGC  CAA  GGC  CAT  GAG  AGG  CAG  TCC  GAG  GGA  TCC  TCC  AGC    754
Glu  Cys  Ser  Ser  Gln  Gly  His  Glu  Arg  Gln  Ser  Glu  Gly  Ser  Ser  Ser
145                      150                      155                      160

CCG  CAG  CTC  CAG  GAG  TCT  GTC  TTC  CAC  CTG  CTG  GTG  CCC  AGT  GTC  ATC    802
Pro  Gln  Leu  Gln  Glu  Ser  Val  Phe  His  Leu  Leu  Val  Pro  Ser  Val  Ile
                    165                      170                      175

CTG  GTC  TTG  CTG  GCC  GTC  GGA  GGC  CTC  TTG  TTC  TAC  AGG  TGG  AGG  CGG    850
Leu  Val  Leu  Leu  Ala  Val  Gly  Gly  Leu  Leu  Phe  Tyr  Arg  Trp  Arg  Arg
               180                      185                      190

CGG  AGC  CAT  CAA  GAG  CCT  CAG  AGA  GCG  GAT  TCT  CCC  TTG  GAG  CAA  CCA    898
Arg  Ser  His  Gln  Glu  Pro  Gln  Arg  Ala  Asp  Ser  Pro  Leu  Glu  Gln  Pro
          195                      200                      205

GAG  GGC  AGC  CCC  CTG  ACT  CAG  GAT  GAC  AGA  CAG  GTG  GAA  CTG  CCA  GTG    946
Glu  Gly  Ser  Pro  Leu  Thr  Gln  Asp  Asp  Arg  Gln  Val  Glu  Leu  Pro  Val
```

|  | 210 |  | 215 |  | 220 |  |
|---|---|---|---|---|---|---|
| TAGAGGGAAT | TCTAAGACCC | CTCACCATCC | TGGACACACT | CGTTTGTCAA | TGTCCCTCTG | 1006 |
| AAAATGTGAC | GCCCAGCCCC | GGACACAGTA | CTCCAGATGT | TGTCTGACCA | GCTCAGAGAG | 1066 |
| AGTACAGTGG | GACTGTTACC | TTCCTTGATA | TGGACAGTAT | TCTTCTATTT | GTGCAGATTA | 1126 |
| AGATTGCATT | AGTTTTTTTC | TTAACAACTG | CATCATACTG | TTGTCATATG | TTGAGCCTGT | 1186 |
| GGTCTATTAA | AACCCCTAGT | TCCATTTCCC | ATAAACTTCT | GTCAAGCCAG | ACCATCTCTA | 1246 |
| CCCTGTACTT | GGACAACTTA | ACTTTTTTAA | CCAAAGTGCA | GTTTATGTTC | ACCTTTGTTA | 1306 |
| AAGCCACCTT | GTGGTTTCTG | CCCATCACCT | GAACCTACTG | AAGTTGTGTG | AAATCCTAAT | 1366 |
| TCTGTCATCT | CCGTAGCCCT | CCCAGTTGTG | CCTCCTGCAC | ATTGATGAGT | GCCTGCTGTT | 1426 |
| GTCTTTGCCC | ATGTTGTTGA | TGTAGCTGTG | ACCCTATTGT | TCCTCACCCC | TGCCCCCCGC | 1486 |
| CAACCCCAGC | TGGCCCACCT | CTTCCCCCTC | CCACCCAAGC | CCACAGCCAG | CCCATCAGGA | 1546 |
| AGCCTTCCTG | GCTTCTCCAC | AACCTTCTGA | CTGCTCTTTT | CAGTCATGCC | CCTCCTGCTC | 1606 |
| TTTTGTATTT | GGCTAATAGT | ATATCAATTT | GCACTT |  |  | 1642 |

( 2 ) INFORMATION FOR SEQ ID NO:4:

( i ) SEQUENCE CHARACTERISTICS:
        ( A ) LENGTH: 256 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met -32 | Thr | Ala -30 | Pro | Gly | Ala | Ala | Gly -25 | Arg | Cys | Pro | Pro | Thr -20 | Thr | Trp | Leu |
|---|---|---|---|---|---|---|---|---|---|---|---|---|---|---|---|
| Gly | Ser -15 | Leu | Leu | Leu | Leu | Val -10 | Cys | Leu | Leu | Ala | Ser -5 | Arg | Ser | Ile | Thr |
| Glu 1 | Glu | Val | Ser | Glu 5 | Tyr | Cys | Ser | His | Met 10 | Ile | Gly | Ser | Gly | His 15 | Leu |
| Gln | Ser | Leu | Gln 20 | Arg | Leu | Ile | Asp | Ser 25 | Gln | Met | Glu | Thr | Ser 30 | Cys | Gln |
| Ile | Thr | Phe 35 | Glu | Phe | Val | Asp | Gln 40 | Glu | Gln | Leu | Lys | Asp 45 | Pro | Val | Cys |
| Tyr | Leu 50 | Lys | Lys | Ala | Phe | Leu 55 | Leu | Val | Gln | Tyr | Ile 60 | Met | Glu | Asp | Thr |
| Met 65 | Arg | Phe | Arg | Asp | Asn 70 | Thr | Pro | Asn | Ala | Ile 75 | Ala | Ile | Val | Gln | Leu 80 |
| Gln | Glu | Leu | Ser | Leu 85 | Arg | Leu | Lys | Ser | Cys 90 | Phe | Thr | Lys | Asp | Tyr 95 | Glu |
| Glu | His | Asp | Lys 100 | Ala | Cys | Val | Arg | Thr 105 | Phe | Tyr | Glu | Thr | Pro 110 | Leu | Gln |
| Leu | Leu | Glu 115 | Lys | Val | Lys | Asn | Val 120 | Phe | Asn | Glu | Thr | Lys 125 | Asn | Leu | Leu |
| Asp | Lys 130 | Asp | Trp | Asn | Ile | Phe 135 | Ser | Lys | Asn | Cys | Asn 140 | Asn | Ser | Phe | Ala |
| Glu 145 | Cys | Ser | Ser | Gln | Gly 150 | His | Glu | Arg | Gln | Ser 155 | Glu | Gly | Ser | Ser | Ser 160 |
| Pro | Gln | Leu | Gln | Glu 165 | Ser | Val | Phe | His | Leu 170 | Leu | Val | Pro | Ser | Val 175 | Ile |
| Leu | Val | Leu | Leu 180 | Ala | Val | Gly | Gly | Leu 185 | Leu | Phe | Tyr | Arg | Trp 190 | Arg | Arg |

```
Arg Ser His Gln Glu Pro Gln Arg Ala Asp Ser Pro Leu Glu Gln Pro
        195                 200                 205

Glu Gly Ser Pro Leu Thr Gln Asp Asp Arg Gln Val Glu Leu Pro Val
        210                 215                 220
```

( 2 ) INFORMATION FOR SEQ ID NO:5:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

( 2 ) INFORMATION FOR SEQ ID NO:6:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110
```

```
          Thr  Ile  Val  Glu  Phe  Leu  Asn  Arg  Trp  Ile  Thr  Phe  Ser  Gln  Ser  Ile
                    115                      120                      125

Ile  Ser  Thr  Leu  Thr
                    130
```

( 2 ) INFORMATION FOR SEQ ID NO:7:

( i ) SEQUENCE CHARACTERISTICS:
        ( A ) LENGTH: 173 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
          Pro  Leu  Gly  Pro  Ala  Ser  Ser  Leu  Pro  Gln  Ser  Phe  Leu  Leu  Lys  Cys
          1                   5                        10                      15

Leu  Glu  Gln  Val  Arg  Lys  Ile  Gln  Gly  Asp  Gly  Ala  Ala  Leu  Gln  Glu
                              20                        25                      30

Lys  Leu  Cys  Ala  Thr  Tyr  Lys  Leu  Cys  His  Pro  Glu  Glu  Leu  Val  Leu
                         35                        40                       45

Leu  Gly  His  Ser  Leu  Gly  Ile  Pro  Trp  Ala  Pro  Leu  Ser  Ser  Cys  Pro
                    50                        55                       60

Ser  Gln  Ala  Leu  Gln  Leu  Ala  Gly  Cys  Leu  Ser  Gln  Leu  His  Ser  Gly
          65                             70                      75                    80

Leu  Phe  Leu  Tyr  Gln  Gly  Leu  Leu  Gln  Ala  Leu  Glu  Gly  Ile  Ser  Pro
                              85                       90                        95

Glu  Leu  Gly  Pro  Thr  Leu  Asp  Thr  Leu  Gln  Leu  Asp  Val  Ala  Asp  Phe
                         100                      105                      110

Ala  Thr  Thr  Ile  Trp  Gln  Gln  Met  Glu  Glu  Leu  Gly  Met  Ala  Pro  Ala
                         115                      120                      125

Leu  Gln  Pro  Thr  Gln  Gly  Ala  Met  Pro  Ala  Phe  Ala  Ser  Ala  Phe  Gln
                    130                      135                      140

Arg  Arg  Ala  Gly  Gly  Val  Leu  Val  Ala  Ser  His  Leu  Gln  Ser  Phe  Leu
          145                       150                      155                      160

Glu  Val  Ser  Tyr  Arg  Val  Leu  Arg  His  Leu  Ala  Gln  Pro
                              165                      170
```

( 2 ) INFORMATION FOR SEQ ID NO:8:

( i ) SEQUENCE CHARACTERISTICS:
        ( A ) LENGTH: 147 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
          Arg  Ser  Leu  Asn  Cys  Thr  Leu  Arg  Asp  Ser  Gln  Gln  Lys  Ser  Leu  Val
          1                   5                        10                      15

Met  Ser  Gly  Pro  Tyr  Glu  Leu  Lys  Ala  Leu  His  Leu  Gln  Gly  Gln  Asp
                              20                       25                        30

Met  Glu  Gln  Gln  Val  Val  Phe  Ser  Met  Ser  Phe  Val  Gln  Gly  Glu  Glu
                         35                       40                        45

Ser  Asn  Asp  Lys  Ile  Pro  Val  Ala  Leu  Gly  Leu  Lys  Glu  Lys  Asn  Leu
                    50                       55                        60

Tyr  Leu  Ser  Cys  Val  Leu  Lys  Asp  Asp  Lys  Pro  Thr  Leu  Gln  Leu  Glu
          65                             70                      75                    80
```

|         |      |      |      | 85   |      |      |      |      | 90   |      |      |      |      | 95   |      |
|---------|------|------|------|------|------|------|------|------|------|------|------|------|------|------|------|
| Ser     | Val  | Asp  | Pro  | Lys  | Asn  | Tyr  | Pro  | Lys  | Lys  | Lys  | Met  | Glu  | Lys  | Arg  | Phe  |
| Val     | Phe  | Asn  | Lys  | Ile  | Glu  | Ile  | Asn  | Asn  | Lys  | Leu  | Glu  | Phe  | Glu  | Ser  | Ala  |
|         |      |      | 100  |      |      |      |      | 105  |      |      |      |      | 110  |      |      |
| Gln     | Phe  | Pro  | Asn  | Trp  | Tyr  | Ile  | Ser  | Thr  | Ser  | Gln  | Ala  | Glu  | Asn  | Met  | Pro  |
|         |      | 115  |      |      |      |      | 120  |      |      |      |      | 125  |      |      |      |
| Val     | Phe  | Leu  | Gly  | Gly  | Thr  | Lys  | Gly  | Gly  | Gln  | Asp  | Ile  | Thr  | Asp  | Phe  | Thr  |
|         | 130  |      |      |      |      | 135  |      |      |      |      | 140  |      |      |      |      |
| Met     | Gln  | Phe  |      |      |      |      |      |      |      |      |      |      |      |      |      |
| 145     |      |      |      |      |      |      |      |      |      |      |      |      |      |      |      |

( 2 ) INFORMATION FOR SEQ ID NO:9:

( i ) SEQUENCE CHARACTERISTICS:
    ( A ) LENGTH: 122 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:9:

| Pro | Tyr | Val | Lys | Glu | Ala | Glu | Asn | Leu | Lys | Lys | Tyr | Phe | Asn | Ala | Gly |
|-----|-----|-----|-----|-----|-----|-----|-----|-----|-----|-----|-----|-----|-----|-----|-----|
| 6   |     |     |     | 10  |     |     |     |     | 15  |     |     |     |     | 20  |     |
| His | Ser | Asp | Val | Ala | Asp | Asn | Gly | Thr | Leu | Phe | Leu | Gly | Ile | Leu | Lys |
|     |     |     | 25  |     |     |     |     | 30  |     |     |     |     | 35  |     |     |
| Asn | Trp | Lys | Glu | Glu | Ser | Asp | Arg | Lys | Ile | Met | Gln | Ser | Gln | Ile | Val |
|     |     | 40  |     |     |     |     | 45  |     |     |     |     | 50  |     |     |     |
| Ser | Phe | Tyr | Phe | Lys | Leu | Phe | Lys | Asn | Phe | Lys | Asp | Asp | Gln | Ser | Ile |
|     | 55  |     |     |     |     | 60  |     |     |     |     | 65  |     |     |     |     |
| Gln | Lys | Ser | Val | Glu | Thr | Ile | Lys | Glu | Asp | Met | Asn | Val | Lys | Phe | Phe |
| 70  |     |     |     |     | 75  |     |     |     |     | 80  |     |     |     |     | 85  |
| Asn | Ser | Asn | Lys | Lys | Lys | Arg | Asp | Asp | Phe | Glu | Lys | Leu | Thr | Asn | Tyr |
|     |     |     |     | 90  |     |     |     |     | 95  |     |     |     |     | 100 |     |
| Ser | Val | Thr | Asp | Leu | Asn | Val | Gln | Arg | Lys | Ala | Ile | His | Glu | Leu | Ile |
|     |     |     | 105 |     |     |     |     | 110 |     |     |     |     | 115 |     |     |
| Gln | Val | Met | Ala | Glu | Leu | Ser | Pro | Ala | Ala |     |     |     |     |     |     |
|     |     | 120 |     |     |     |     | 125 |     |     |     |     |     |     |     |     |